United States Patent [19]
Silverman et al.

[11] Patent Number: 6,028,243
[45] Date of Patent: Feb. 22, 2000

[54] MICE AND CELLS WITH A HOMOZYGOUS DISRUPTION IN THE RNASE L GENE AND METHODS THEREFORE

[75] Inventors: Robert H. Silverman, Beachwood; Aimin Zhou, Solon, both of Ohio

[73] Assignee: The Cleveland Clinic Foundation, Cleveland, Ohio

[21] Appl. No.: 08/943,956

[22] Filed: Oct. 3, 1997

Related U.S. Application Data

[60] Provisional application No. 60/027,656, Oct. 4, 1996.

[51] Int. Cl.$^7$ ............................. C12N 15/11; C12N 15/85; A01K 67/00; G01N 33/00
[52] U.S. Cl. ................................... 800/18; 800/3; 800/21; 435/325; 435/320.1; 435/455; 536/23.1
[58] Field of Search .................................. 800/2, DIG. 1, 800/21, 3, 18; 536/23.1; 435/320.1, 325, 455

[56] References Cited

FOREIGN PATENT DOCUMENTS

WO 94/20605   9/1995   WIPO.

OTHER PUBLICATIONS

Bradley et al. Modifying the mouse: design and desire. Biotechnology, vol. 10, pp. 534–539, May 1992.
Mullins and Mullins. Perspectives Series: Molecular Medicine in genetically engineered animals, transgenesis in the rat and larger animals. J. Clin.Invest., vol. 98, pp. S37–S40, 1996.
Seamark. Progress and emerging problems in livestock transgenesis: a summary perspective. Reprod. Feril. Dev., vol. 6, pp. 653–657, 1994.
Mons et al. Defects in heart and lung development in compound heterozygotes for two different targeted mutation at the N–myc locus. Development, vol. 119, pp. 485–499, Oct. 1993
Silverman. 2–5A–dependent RNase L: a regulated endoribonecluase in the interferon system. Ribonucleases. Academic, N.Y.,N.Y., pp. 515–551, 1997.
Capecchi. Targeted gene replacement. Scientific american, vol. 270, pp. 34–41, Mar. 1994.
"Expression Cloning of 2–5A–Dependent RNase: A Uniquely Regulated Mediator of Interferon Activation", by Zhou, et al., *Cell*, vol. 72, Mar. 12, 1993, pp. 753–765.

"2–5A–dependent RNase Molecules Dimerize during Activation by 2–5A*" by Dong, et al., *J. Bio Chem.*, vol. 270, No. 8, Feb. 24, 1995, pp. 4133–4137.
"A dominant negative mutant of 2–5A–dependent RNase suppresses antiprolifereative and antiviral effects of interferon" by Hassel, et al., *EMBO Journal*, vol. 12, No. 8, 1993, pp. 3297–3304.
"Localization of the Ribonuclease L Inhibitor Gene (RNS41), a New Member of the Interferon–Regulated 2–5A Pathway, to 4q31 by Fluorescence in Situ Hybridization" by Diriong, et al., *Genomics*, vol. 32, 1996, pp. 448–490.
"Catalytic Cleavage of an RNA Target by 2–5A Antisense and RNase L*" by Maitra, et al., *J. Bio. Chem.*, vol. 270, No. 25, Jun. 22, 1995, pp. 15071–15075.
"Cloning and Characterization of a RNase L Inhibitor: A new Component of the Interferon–Regulated 2–5A Pathway" by Bisbal, et al., *J. Bio. Chem.*, vol. 270, No. 22, Jun. 2, 1996; pp. 13308–13317.
"Induction of interferon regulatory factors, 2'–5' oligoadenylate synthetase, P68 kinase and RNase L in chronic myelogenous leukaemia cells and its relationship to clinical responsiveness" by Fischer, et al., *Brit. J. Haematology*, 1996, vol. 92, pp. 595–603.
"Chromosomal Localization and expression pattern of the RNase L inhibitor gene", by Aubry, et al., *FEBS Letters*, vol. 381, 1996, pp.135–139.
"Activation of interferon–regulated, dsRNA–dependent enzymes by human immunodeficiency virus–1 leader RNA", by SenGupta, et al., *Nucleic Acids Research*, vol. 17, No. 3, 1989, pp. 969–978.

*Primary Examiner*—Deborah Crouch
*Assistant Examiner*—Michael C. Wilson
*Attorney, Agent, or Firm*—Calfee, Halter & Griswold LLP

[57] ABSTRACT

The present invention provides a mutant, non-human mammal, particularly a mutant mouse, having a homozygous disruption in the RNase L gene thereof. Since the homozygous disruption in the RNase L gene leads to minimal if any production of RNase L in the mutant mammals, such mutant mammals are useful for assessing the effect of antiviral drugs on the induction, synthesis, or activation of RNase L. The present invention also relates to mutant, non-human, embryonic stem cell lines having a heterozygous disruption of the RNase L gene thereof, to isolated mammalian cells having a homozygous disruption in the RNase L gene thereof, and to a DNA construct comprising a DNA sequence of a disrupted coding exon of a RNase L gene.

14 Claims, 20 Drawing Sheets

A.

B.

Gene Targeting of the Murine RNase L Gene Analyzed by a Southern Blot of Tail DNA Genotype: +/+  +/-  -/-
          1    2    3

Wild Type Allele →
Mutant Allele →

32p-2-5A Crosslinking Assay Shows an Absence of RNase L in Organs of RNase L−/− Mice Mice: RNase L−/−    RNase L+/+

Liver Spleen Kidney Heart Testis   Liver Spleen Kidney Heart Testis
  1     2     3     4     5        6     7     8     9    10

200 —

RNase L → 98 =

```
        -103 aatcccaacttacactcaaagct
     tctttgattaagtgctaggagataaatttgcatttcctca
     aggaaaaggctaaaagtggtagcaggtggcatttaccgtc
```

| | | | | | | | | | |
|---|---|---|---|---|---|---|---|---|---|
| ATG | GAG | AGC | AGG | GAT | CAT | AAC | AAC | CCC | CAG | 30 |
| Met | Glu | Ser | Arg | Asp | His | Asn | Asn | Pro | Gln | 10 |
| | | | | | | | | | |
| GAG | GGA | CCC | ACG | TCC | TCC | AGC | GGT | AGA | AGG | 60 |
| Glu | Gly | Pro | Thr | Ser | Ser | Ser | Gly | Arg | Arg | 20 |
| | | | | | | | | | |
| GCT | GCA | GTG | GAA | GAC | AAT | CAC | TTG | CTG | ATT | 90 |
| Ala | Ala | Val | Glu | Asp | Asn | His | Leu | Leu | Ile | 30 |
| | | | | | | | | | |
| AAA | GCT | GTT | CAA | AAC | GAA | GAT | GTT | GAC | CTG | 120 |
| Lys | Ala | Val | Gln | Asn | Glu | Asp | Val | Asp | Leu | 40 |
| | | | | | | | | | |
| GTC | CAG | CAA | TTG | CTG | GAA | GGT | GGA | GCC | AAT | 150 |
| Val | Gln | Gln | Leu | Leu | Glu | Gly | Gly | Ala | Asn | 50 |
| | | | | | | | | | |
| GTT | AAT | TTC | CAG | GAA | GAG | GAA | GGG | GGC | TGG | 180 |
| Val | Asn | Phe | Gln | Glu | Glu | Glu | Gly | Gly | Trp | 60 |
| | | | | | | | | | |
| ACA | CCT | CTG | CAT | AAC | GCA | GTA | CAA | ATG | AGC | 210 |
| Thr | Pro | Leu | His | Asn | Ala | Val | Gln | Met | Ser | 70 |
| | | | | | | | | | |
| AGG | GAG | GAC | ATT | GTG | GAA | CTT | CTG | CTT | CGT | 240 |
| Arg | Glu | Asp | Ile | Val | Glu | Leu | Leu | Leu | Arg | 80 |
| | | | | | | | | | |
| CAT | GGT | GCT | GAC | CCT | GTT | CTG | AGG | AAG | AAG | 270 |
| His | Gly | Ala | Asp | Pro | Val | Leu | Arg | Lys | Lys | 90 |
| | | | | | | | | | |
| AAT | GGG | GCC | ACG | CTT | TTT | ATC | CTC | GCA | GCG | 300 |
| Asn | Gly | Ala | Thr | Leu | Phe | Ile | Leu | Ala | Ala | 100 |
| | | | | | | | | | |
| ATT | GCG | GGG | AGC | GTG | AAG | CTG | CTG | AAA | CTT | 330 |
| Ile | Ala | Gly | Ser | Val | Lys | Leu | Leu | Lys | Leu | 110 |
| | | | | | | | | | |
| TTC | CTT | TCT | AAA | GGA | GCA | GAT | GTC | AAT | GAG | 360 |
| Phe | Leu | Ser | Lys | Gly | Ala | Asp | Val | Asn | Glu | 120 |
| | | | | | | | | | |
| TGT | GAT | TTT | TAT | GGC | TTC | ACA | GCC | TTC | ATG | 390 |
| Cys | Asp | Phe | Tyr | Gly | Phe | Thr | Ala | Phe | Met | 130 |
| | | | | | | | | | |
| GAA | GCC | GCT | GTG | TAT | GGT | AAG | GTC | AAA | GCC | 420 |
| Glu | Ala | Ala | Val | Tyr | Gly | Lys | Val | Lys | Ala | 140 |
| | | | | | | | | | |
| CTA | AAA | TTC | CTT | TAT | AAG | AGA | GGA | GCA | AAT | 450 |
| Leu | Lys | Phe | Leu | Tyr | Lys | Arg | Gly | Ala | Asn | 150 |
| | | | | | | | | | |
| GTG | AAT | TTG | AGG | CGA | AAG | ACA | AAG | GAG | GAT | 480 |
| Val | Asn | Leu | Arg | Arg | Lys | Thr | Lys | Glu | Asp | 160 |
| | | | | | | | | | |
| CAA | GAG | CGG | CTG | AGG | AAA | GGA | GGG | GCC | ACA | 510 |
| Gln | Glu | Arg | Leu | Arg | Lys | Gly | Gly | Ala | Thr | 170 |

Fig. 12 (con't)

```
GCT CTC ATG GAC GCT GCT GAA AAA GGA CAC        540
Ala Leu Met Asp Ala Ala Glu Lys Gly His        180

GTA GAG GTC TTG AAG ATT CTC CTT GAT GAG        570
Val Glu Val Leu Lys Ile Leu Leu Asp Glu        190

ATG GGG GCA GAT GTA AAC GCC TGT GAC AAT        600
Met Gly Ala Asp Val Asn Ala Cys Asp Asn        200

ATG GGC AGA AAT GCC TTG ATC CAT GCT CTC        630
Met Gly Arg Asn Ala Leu Ile His Ala Leu        210

CTG AGC TCT GAC GAT AGT GAT GTG GAG GCT        660
Leu Ser Ser Asp Asp Ser Asp Val Glu Ala        220

ATT ACG CAT CTG CTG CTG GAC CAT GGG GCT        690
Ile Thr His Leu Leu Leu Asp His Gly Ala        230

GAT GTC AAT GTG AGG GGA GAA AGA GGG AAG        720
Asp Val Asn Val Arg Gly Glu Arg Gly Lys        240

ACT CCC CTG ATC CTG GCA GTG GAG AAG AAG        750
Thr Pro Leu Ile Leu Ala Val Glu Lys Lys        250

CAC TTG GGT TTG GTG CAG AGG CTT CTG GAG        780
His Leu Gly Leu Val Gln Arg Leu Leu Glu        260

CAA GAG CAV ATA GAG ATT AAT GAC ACA GAC        810
Gln Glu His Ile Glu Ile Asn Asp Thr Asp        270

AGT GAT GGC AAA ACA GCA CTG CTG CTT GCT        840
Ser Asp Gly Lys Thr Ala Leu Leu Leu Ala        280

GTT GAA CTC AAA CTG AAG AAA ATC GCC GAG        870
Val Glu Leu Lys Leu Lys Lys Ile Ala Glu        290

TTG CTG TGC AAA CGT GGA GCC AGT ACA GAT        900
Leu Leu Cys Lys Arg Gly Ala Ser Thr Asp        300

TGT GGG GAT CTT GTT ATG ACA GCG AGG CGG        930
Cys Gly Asp Leu Val Met Thr Ala Arg Arg        310

AAT TAT GAC CAT TCC CTT GTG AAG GTT CTT        960
Asn Tyr Asp His Ser Leu Val Lys Val Leu        320

CTC TCT CAT GGA GCC AAA GAA GAT TTT CAC        990
Leu Ser His Gly Ala Lys Glu Asp Phe His        330

CCT CCT GCT GAA GAC TGG AAG CCT CAG AGC        1020
Pro Pro Ala Glu Asp Trp Lys Pro Gln Ser        340

TCA CAC TGG GGG GCA GCC CTG AAG GAT CTC        1050
Ser His Trp Gly Ala Ala Leu Lys Asp Leu        350
```

Fig. 12 (con't)

```
CAC AGA ATA TAC CGC CCT ATG ATT GGC AAA    1080
His Arg Ile Tyr Arg Pro Met Ile Gly Lys     360

CTC AAG TTC TTT ATT GAT GAA AAA TAC AAA    1110
Leu Lys Phe Phe Ile Asp Glu Lys Try Lys     370

ATT GCT GAT ACT TCA GAA GGA GGC ATC TAC    1140
Ile Ala Asp Thr Ser Glu Gly Gly Ile Tyr     380

CTG GGG TTC TAT GAG AAG CAA GAA GTA GCT    1170
Leu Gly Phe Tyr Glu Lys Gln Glu Val Ala     390

GTG AAG ACG TTC TGT GAG GGC AGC CCA CGT    1200
Val Lys Thr Phe Cys Glu Gly Ser Pro Arg     400

GCA CAG CGG GAA GTC TCT TGT CTG CAA AGC    1230
Ala Gln Arg Glu Val Ser Cys Leu Gln Ser     410

AGC CGA GAG AAC AGT CAC TTG GTG ACA TTC    1260
Ser Arg Glu Asn Ser His Leu Val Thr Phe     420

TAT GGG AGT GAG AGC CAC AGG GGC CAC TTG    1290
Tyr Gly Ser Glu Ser His Arg Gly His Leu     430

TTT GTG TGT GTC ACC CTC TGT GAG CAG ACT    1320
Phe Val Cys Val Thr Leu Cys Glu Gln Thr     440

CTG GAA GCG TGT TTG GAT GTG CAC AGA GGG    1350
Leu Glu Ala Cys Leu Asp Val His Arg Gly     450

GAA GAT GTG GAA AAT GAG GAA GAT GAA TTT    1380
Glu Asp Val Glu Asn Glu Glu Asp Glu Phe     460

GCC CGA AAT GTC CTG TCA TCT ATA TTT AAG    1410
Ala Arg Asn Val Lue Ser Ser Ile Phe Lys     470

GCT GTT CAA GAA CTA CAC TTG TCC TGT GGA    1440
Ala Val Gln Glu Leu His Leu Ser Cys Gly     480

TAC ACC CAC CAG GAT CTG CAA CCA CAA AAC    1470
Tyr Thr His Gln Asp Leu Gln Pro Gln Asn     490

ATC TTA ATA GAT TCT AAG AAA GCT GCT CAC    1500
Ile Leu Ile Asp Ser Lys Lys Ala Ala His     500

CTG GCA GAT TTT GAT AAG AGC ATC AAG TGG    1530
Leu ala Asp Phe Asp Lys Ser Ile Lys Trp     510

GCT GGA GAT CCA CAG GAA GTC AAG AGA GAT    1560
Ala Gly Asp Pro Gln Glu Val Lys Arg Asp     520

CTA GAG GAC CTT GGA CGG CTG GTC CTC TAT    1590
Leu Glu Asp Leu Gly Arg Leu Val Leu Tyr     530

GTG GTA AAG AAG GGA AGC ATC TCA TTT GAG    1620
Val Val Lys Lys Gly Ser Ile Ser Phe Glu     540
```

Fig. 12 (con't)

```
GAT CTG AAA GCT CAA AGT AAT GAA GAG GTG        1650
Asp Leu Lys Ala Gln Ser Asn Glu Glu Val         550

GTT CAA CTT TCT CCA GAT GAG GAA ACT AAG        1680
Val Gln Leu Ser Pro Asp Glu Glu Thr Lys         560

GAC CTC ATT CAT CGT CTC TTC CAT CCT GGG        1710
Asp Leu Ile His Arg Leu Phe His Pro Gly         570

GAA CAT GTG AGG GAC TGT CTG AGT GAC CTG        1740
Glu His Val Arg Asp Cys Leu Ser Asp Leu         580

CTG GGT CAT CCC TTC TTT TGG ACT TGG GAG        1770
Leu Gly His Pro Phe Phe Trp Thr Trp Glu         590

AGC CGC TAT AGG ACG CTT CGG AAT GTG GGA        1800
Ser Arg Tyr Arg Thr Leu Arg Asn Val Gly         600

AAT GAA TCC GAC ATC AAA ACA CGA AAA TCT        1830
Asn Glu Ser Asp Ile Lys Thr Arg Lys Ser         610

GAA AGT GAG ATC CTC AGA CTA CTG CAA CCT        1860
Glu Ser Glu Ile Leu Arg Leu Leu Gln Pro         620

GGG CCT TCT GAA CAT TCC AAA AGT TTT GAC        1890
Gly Pro Ser Glu His Ser Lys Ser Phe Asp         630

AAG TGG ACG ACT AAG ATT AAT GAA TGT GTT        1920
Lys Trp Thr Thr Lys Ile Asn Glu Cys Val         640

ATG AAA AAA ATG AAT AAG TTT TAT GAA AAA        1950
Met Lys Lys Met Asn Lys Phe Tyr Glu Lys         650

AGA GGC AAT TTC TAC CAG AAC ACT GTG GGT        1980
Arg Gly Asn Phe Tyr Gln Asn Thr Val Gly         660

GAT CTG CTA AAG TTC ATC CGG AAT TTG GGA        2210
Asp Leu Leu Lys Phe Ile Arg Asn Leu Gly         670

GAA CAC ATT GAT GAA GAA AAG CAT AAA AAG        2040
Glu His Ile Asp Glu Glu Lys His Lys Lys         680

ATG AAA TTA AAA ATT GGA GAC CCT TCC CTG        2070
Met Lys Leu Lys Ile Gly Asp Pro Ser Leu         690

TAT TTT CAG AAG ACA TTT CCA GAT CTG GTG        2100
Tyr Phe Gln Lys Thr Phe Pro Asp Leu Val         700

ATC TAT GTC TAC ACA AAA CTA CAG AAC ACA        2130
Ile Tyr Val Tyr Thr Lys Leu Gln Asn Thr         710

GAA TAT AGA AAG CAT TTC CCC CAA ACC CAC        2160
Glu Tyr Arg Lys His Phe Pro Gln Thr His         720
```

Fig. 12 (con't)

```
AGT CCA AAC AAA CCT CAG TGT GAT GGA GCT       2190
Ser Pro Asn Lys Pro Gln Cys Asp Gly Ala        730

GGT GGG GCC AGT GGG TTG GCC AGC CCT GGG       2220
Gly Gly Ala Ser Gly Leu Ala Ser Pro Gly        740

TGC 2223    tgatgactgatttgctggagttcagggaactact 2258
Cys  741
```

| | |
|---|---:|
| tattagctgtagagtccttggcaaatcacaacat | 2292 |
| tctgggccttttaactcaccaggttgcttgtgagggat | 2330 |
| gagttgcatagctgatatgtcagtccctggcatcgtg | 2367 |
| tattccatatgtctataacaaaagcaatatatacccag | 2405 |
| actacactagtccataagctttacccactaactggga | 2442 |
| ggacattctgctaagattccttttgtcaattgcaccaa | 2480 |
| aagaatgagtgccttgacccctaatgctgcatatgtt | 2517 |
| acaattctctcacttaattttcccaatgatcttgcaaa | 2555 |
| acaggattatcatcccatttaagaactgaggaacc | 2592 |
| tgagactcagagagtgtgagctactggcccaagattat | 2630 |
| tcaatttatacctagcactttataaatttatgtggtg | 2667 |
| ttattggtacctctcatttgggcaccttaaaacttaac | 2705 |
| tatcttccagggctcttccagatgaggcccaaaacat | 2742 |
| atataggggttccaggaatctcattcattcattcagta | 2780 |
| tttattgagcatctagtataagtctgggcactggatg | 2817 |
| catgaatt | 2825 |

Fig. 13

```
-163
attcggcacgaggaaggtgccaattactagctcccttctttattcgtgta ctgatgagatgtcagaagacagaacataatcagcccaatccctactccaa gactctcattgtgtcccaaagaaacacgtgtgcatttcccaaggaaaa
```

| ggcattgaggacc | ATG GAG ACC CCG GAT TAT | 18 |
|---|---|---|
| | Met Glu Thr Pro Asp Tyr | 6 |

| AAC ACA CCT CAG GGT GGA ACC CCA TCA GCG | 48 |
|---|---|
| Asn Thr Pro Gln Gly Gly Thr Pro Ser Ala | 16 |

| GGA AGT CAG AGG ACC GTT GTC GAA GAT GAT | 78 |
|---|---|
| Gly Ser Gln Arg Thr Val Val Glu Asp Asp | 26 |

| TCT TCG TTG ATC AAA GCT GTT CAG AAG GGA | 108 |
|---|---|
| Ser Ser Leu Ile Lys Ala Val Gln Lys Gly | 36 |

| GAT GTT GTC AGG GTC CAG CAA TTG TTA GAA | 138 |
|---|---|
| Asp Val Val Arg Val Gln Gln Leu Leu Glu | 46 |

| AAA GGG GCT GAT GCC AAT GCC TGT GAA GAC | 268 |
|---|---|
| Lys Gly Ala Asp Ala Asn Ala Cys Glu Asp | 56 |

| ACC TGG GGC TGG ACA CCT TTG CAC AAC GCA | 198 |
|---|---|
| Thr Trp Gly Trp Thr Pro Leu His Asn Ala | 66 |

| GTG CAA GCT GGC AGG GTA GAC ATT GTG AAC | 228 |
|---|---|
| Val Gln Ala Gly Arg Val Asp Ile Val Asn | 76 |

| CTC CTG CTT AGT CAT GGT GCT GAC CCT CAT | 258 |
|---|---|
| Leu Leu Leu Ser His Gly Ala Asp Pro His | 86 |

| CGG AGG AAG AAG AAT GGG GCC ACC CCC TTC | 288 |
|---|---|
| Arg Arg Lys Lys Asn Gly Ala Thr Pro Phe | 96 |

| ATC ATT GCT GGG ATC CAG GGA GAT GTG AAA | 318 |
|---|---|
| Ile Ile Ala Gly Ile Gln Gly Asp Val Lys | 106 |

| CTG CTC GAG ATT CTC CTC TCT TGT GGT GCA | 348 |
|---|---|
| Leu Leu Glu Ile Leu Leu Ser Cys Gly Ala | 116 |

| GAC GTC AAT GAG TGT GAC GAG AAC GGA TTC | 378 |
|---|---|
| Asp Val Asn Glu Cys Asp Glu Asn Gly Phe | 126 |

| ACG GCT TTC ATG GAA GCT GCT GAG CGT GGT | 408 |
|---|---|
| Thr Ala Phe Met Glu Ala Ala Glu Arg Gly | 136 |

| AAC GCT GAA GCC TTA AGA TTC CTT TTT GCT | 438 |
|---|---|
| Asn Ala Glu Ala Leu Arg Phe Leu Phe Ala | 146 |

| AAG GGA GCC AAT GTG AAT TTG CGA CGA CAG | 468 |
|---|---|
| Lys Gly Ala Asn Val Asn Leu Arg Arg Gln | 156 |

Fig. 13 (con't)

| | | | | | | | | | | |
|---|---|---|---|---|---|---|---|---|---|---|
| ACA | ACG | AAG | GAC | AAA | AGG | CGA | TTG | AAG | CAA | 498 |
| Thr | Thr | Lys | Asp | Lys | Arg | Arg | Leu | Lys | Gln | 166 |
| GGA | GGC | GCC | ACA | GCT | CTC | ATG | AGC | GCT | GCT | 528 |
| Gly | Gly | Ala | Thr | Ala | Leu | Met | Ser | Ala | Ala | 176 |
| GAG | AAG | GGC | CAC | CTG | GAA | GTC | CTG | AGA | ATT | 558 |
| Glu | Lys | Gly | His | Leu | Glu | Val | Leu | Arg | Ile | 186 |
| CTC | CTC | AAT | GAC | ATG | AAG | GCA | GAA | GTC | GAT | 588 |
| Leu | Leu | Asn | Asp | Met | Lys | Ala | Glu | Val | Asp | 196 |
| GCT | CGG | GAC | AAC | ATG | GGC | AGA | AAT | GCC | CTG | 618 |
| Ala | Arg | Asp | Asn | Met | Gly | Arg | Asn | Ala | Leu | 206 |
| ATC | CGT | ACT | CTG | CTG | AAC | TGG | GAT | TGT | GAA | 648 |
| Ile | Arg | Thr | Leu | Leu | Asn | Trp | Asp | Cys | Glu | 216 |
| AAT | GTG | GAG | GAG | ATT | ACT | TCA | ATC | CTG | ATT | 678 |
| Asn | Val | Glu | Glu | Ile | Thr | Ser | Ile | Leu | Ile | 226 |
| CAG | CAC | GGG | GCT | GAT | GTT | AAC | GTG | AGA | GAA | 708 |
| Gln | His | Gly | Ala | Asp | Val | Asn | Val | Arg | Gly | 236 |
| GAA | AGA | GGG | AAA | ACA | CCC | CTC | ATC | GCA | GCA | 738 |
| Glu | Arg | Gly | Lys | Thr | Pro | Leu | Ile | Ala | Ala | 246 |
| GTG | GAG | AGG | AAG | CAC | ACA | GGC | TTG | GTG | CAG | 768 |
| Val | Glu | Arg | Lys | His | Thr | Gly | Leu | Val | Gln | 256 |
| ATG | CTC | CTG | AGT | CGG | GAA | GGC | ATA | AAC | ATA | 798 |
| Met | Leu | Leu | Ser | Arg | Glu | Gly | Ile | Asn | Ile | 266 |
| GAT | GCC | AGG | GAT | AAC | GAG | GGC | AAG | ACA | GCT | 828 |
| Asp | Ala | Arg | Asp | Asn | Glu | Gly | Lys | Thr | Ala | 276 |
| CTG | CTA | ATT | GCT | GTT | GAT | AAA | CAA | CTG | AAG | 858 |
| Leu | Leu | Ile | Ala | Val | Asp | Lys | Gln | Lue | Lys | 286 |
| GAA | ATT | GTC | CAG | TTG | CTT | CTT | GAA | AAG | GGA | 888 |
| Glu | Ile | Val | Gln | Leu | Leu | Leu | Glu | Lys | Gly | 296 |
| GCT | GAT | AAG | TGT | GAC | GAT | CTT | GTT | TGG | ATA | 918 |
| Ala | Asp | Lys | Cys | Asp | Asp | Leu | Val | Trp | Ile | 306 |
| GCC | AGG | AGG | AAT | CAT | GAC | TAT | CAC | CTT | GTA | 948 |
| Ala | Arg | Arg | Asn | His | Asp | Tyr | His | Leu | Val | 316 |
| AAG | CTT | CTC | CTC | CTT | TAT | GTA | GCT | AAT | CCT | 978 |
| Lys | Leu | Leu | Leu | Pro | Tyr | Val | Ala | Asn | Pro | 326 |
| GAC | ACC | GAC | CCT | CCT | GCT | GGA | GAC | TGG | TCG | 1008 |
| Asp | Thr | Asp | Pro | Pro | Ala | Gly | Asp | Trp | Ser | 336 |

Fig. 13 (con't)

```
CCT CAC AGT TCA CGT TGG GGG ACA GCC TTG          1038
Pro His Ser Ser Arg Trp Gly Thr Ala Lue           346

AAA AGC CTC CAC AGT ATG ACT CGA CCC ATG          1068
Lys Ser Leu His Ser Met Thr Arg Pro Met           356

ATT GGC AAA CTC AAG ATC TTC ATT CAT GAT          1098
Ile Gly Lys Leu Lys Ile Phe Ile His Asp           366

GAC TAT AAA ATT GCT GGC ACT TCC GAA GGG          1128
Asp Tyr Lys Ile Ala Gly Thr Ser Glu Gly           376

GCT GTC TAC CTA GGG ATC TAT GAC AAT CGA          1158
Ala Val Tyr Leu Gly Ile Tyr Asp Asn Arg           386

GAA GTG GCT GTG AAG GTC TTC CGT GAG AAT          1188
Glu Val Ala Val Lys Val Phe Arg Glu Asn           396

AGC CCA CGT GGA TGT AAG GAA GTC TCT TGT          1218
Ser Pro Arg Gly Cys Lys Glu Val Ser Cys           406

CTG CGG GAC TGC GGT GAC CAC AGT AAC TTA          1248
Leu Arg Asp Cys Gly Asp His Ser Asn Leu           416

GTG GCT TTC TAT GGA AGA GAG GAC GAT AAG          1278
Val Ala Phe Tyr Gly Arg Glu Asp Asp Lys           426

GGC TGT TTA TAT GTG TGT GTG TCC CTG TGT          1308
Gly Cys Leu Tyr Val Cys Val Ser Leu Cys           436

GAG TGG ACA CTG GAA GAG TTC CTG AGG TTG          1338
Glu Trp Thr Lue Glu Glu Phe Leu Arg Leu           446

CCC AGA GAG GAA CCT GTG GAG AAC GGG GAA          1368
Pro Arg Glu Glu Pro Val Glu Asn Gly Glu           456

GAT AAG TTT GCC CAC AGC ATC CTA TTA TCT          1398
Asp Lys Phe Ala His Ser Ile Leu Leu Ser           466

ATA TTT GAG GGT GTT CAA AAA CTA CAC TTG          1428
Ile Phe Glu Gly Val Gln Lys Leu His Leu           476

CAT GGA TAT TCC CAT CAG GAC CTG CAA CCA          1458
His Gly Tyr Ser His Gln Asp Leu Gln Pro           486

CAA AAC ATC TTA ATA GAT TCC AAG AAA GCT          1488
Gln Asn Ile Leu Ile Asp Ser Lys Lys Ala           496

GTC CGG CTG GCA GAT TTT GAT CAG AGC ATC          1518
Val Arg Leu Ala Asp Phe Asp Gln Ser Ile           506

CGA TGG ATG GGA GAG TCA CAG ATG GTC AGG          1548
Arg Trp Met Gly Glu Ser Gln Met Val Arg           516

AGA GAC TTG GAG GAT CTT GGA CGG CTG GTT          1578
Arg Asp Leu Glu Asp Leu Gly Arg Leu Val           526
```

Fig. 13 (con't)

```
CTC TAC GTG GTA ATG AAA GGT GAG ATC CCC        1608
Leu Tyr Val Val Met Lys Gly Glu Ile Pro         536

TTT GAG ACA CTA AAG ACT CAG AAT GAT GAA        1638
Phe Glu Ghr Leu Lys Thr Gln Asn Asp Glu         546

GTG CTG CTT ACA ATG TCT CCA GAT GAG GAG        1668
Val Leu Leu Thr Met Ser Pro Asp Glu Glu         556

ACT AAG GAC CTC ATT CAT TGC CTG TTT TCT        1698
Thr Lys Asp Leu Ile His Cys Leu Phe Ser         566

CCT GGA GAA AAT GTC AAG AAC TGC CTG GTA        1728
Pro Gly Glu Asn Val Lys Asn Cys Leu Val         576

GAC CTG CTT GGC CAT CCT TTC TTT TGG ACT        1758
Asp Leu Leu Gly His Pro Phe Phe Trp Thr         586

TGG GAG AAC CGC TAT AGA ACA CTC CGG AAT        1788
Trp Glu Asn Arg Tyr Arg Thr Leu Arg Asn         596

GTG GGA AAT GAA TCT GAC ATC AAA GTA CGG        1818
Val Gly Asn Glu Ser Asp Ile lys Val Arg         606

AAA TGT AAA AGT GAT CTT CTC AGA CTA CTG        1848
Lys Cys Lys Ser Asp Leu Leu Arg Leu Leu         616

CAG CAT CAG ACA CTT GAG CCT CCC AGA AGC        1878
Gln His Gln Thr Leu Glu Pro Pro Arg Ser         626

TTT GAC CAG TGG ACA TGT AAG ATC GAC AAA        1908
Phe Asp Gln Trp Thr Ser Lys Ile Asp Lys         636

AAT GTT ATG GAT GAA ATG AAT CAT TTC TAC        1938
Asn Val Met Asp Glu Met Asn His Phe Tyr         646

GAA AAG AGA AAA AAA AAC CCT TAT CAG GAT        1968
Glu Lys Arg Lys Lys Asn Pro Tyr Gln Asp         656

ACT GTA GGT GAT CTG CTG AAG TTT ATT CGG        1998
Thr Val Gly Asp Leu Leu Lys Phe Ile Arg         666

AAT ATA GGC GAA CAC ATC AAT GAG GAA AAA        2028
Asn Ile Gly Glu His Ile Asn Glu Glu Lys         676

AAG CGG GGG                                     2037
Lys Arg Gly                                     679
```

MICE AND CELLS WITH A HOMOZYGOUS DISRUPTION IN THE RNASE L GENE AND METHODS THEREFORE

This application claims the benefit of U.S. Provisional Application No. 60/027,656 filed Oct. 4, 1996.

The present invention was made with support from National Institutes of Health Grant NO. CA44059-14. The United States Government has certain rights in the invention.

BACKGROUND

RNase L is a mammalian enzyme that has been implicated in the antiviral effect of the antiviral agent interferon against certain viruses including encephalomyocarditis virus (ECMV), reovirus, and vaccinia virus. It has been shown that treatment of mammalian cells with the antiviral agent interferon induces transcription of the RNase L gene. Treatment with interferon also induces transcription of a set of genes encoding at least four different species of 2-5A synthetase, an enzyme involved in the synthesis of the allosteric effectors that activate the RNase L enzyme. Upon activation, RNase L breaks down both viral and cellular RNA, thus, crippling the ability of the cell to produce progeny virus.

Drugs which activate the RNase L enzyme have the potential to be used as antiviral and cancer chemotherapy agents. Thus, efforts are currently underway to identify antiviral drugs which are capable of specifically and directly stimulating the synthesis of RNase L or the activation of RNase L via the 2-5A system. However, at present there are very few tools which are useful for directly assessing the effect of antiviral drugs that activate RNase L. The most widely used assay is one which monitors the appearance of specific rRNA cleavage products in virus-infected cells following treatment with the drug. However, this assay is difficult and tedious to perform and not always reliable.

Thus, it is desirable to have a new research tool which is useful for determining whether a given antiviral drug is capable of inducing the synthesis or activation of RNase L.

SUMMARY OF THE INVENTION

The present invention provides a novel, mutant, non-human mammal useful for assessing the effect of antiviral drugs on the induction, synthesis, and activation of RNase L. The mutant mammal, preferably a rodent, has a homozygous disruption of the RNase L gene of the mammal's somatic cells and germ cells. As used herein "disruption" means an addition of nucleotides to the wild-type RNase L gene of the mammal or a deletion of nucleotides from the wild type RNase L gene of the mammal. Preferably, the homozygous disruption in the RNase L gene of the mutant mammal is in a coding exon of the RNase L gene, more preferably between codons 23 and 720.

The present invention also provides mutant isolated mammalian embryonic stem cell lines having a heterozygous disruption in the RNase L genes thereof. Such cells are useful for making the mutant non-human mammals. The present invention also provides a DNA construct comprising a partial or full coding exon sequence of a mammalian RNase L gene, with the coding exon having a disruption therein. The present invention further relates to isolated mammalian cells having a homozygous disruption in the RNase L genes thereof. The present invention also relates to a method of using isolated mammalian cells having a homozygous disruption in the RNase L genes thereof and of using the mutant mammals of the present invention to determine the involvement of the 2-5A system in the antiviral effect of an anitviral drug. The method comprises the steps of treating the cells or animals with the drug; infecting the animals or cells with a virus known to be susceptible to the antiviral effect of interferon; and assessing the effect of the antiviral effect of the drug on the mutant cells or mammals.

BRIEF DESCRIPTION OF THE FIGURES

The file of this patent contains at least one black and white photograph. Copies of this patent with black and white photographs will be provided by the Patent and Trademark Office upon request and payment of the necessary fee.

FIG. 7 (lower panel) shows the binding of radiolabeled 2-5A to protein extracted from wild-type and RNase-null mice.

FIG. 12 shows the nucleotide sequence of human RNase L cDNA, SEQ ID NO: 1, and the predicted amino acid sequence, SEQ ID NO: 2, of the human RNase L enzyme.

FIG. 13 shows the nucleotide sequence of mouse RNase L cDNA, SEQ ID NO:3, and the predicted amino acid sequence, SEQ ID NO: 4, of the mouse RNase L enzyme.

DETAILED DESCRIPTION OF THE INVENTION

In accordance with the present invention, a mutant non-human mammal useful for assessing the effect of antiviral drugs on the induction, synthesis, and activation of the RNase L enzyme is provided. The mutant mammals of the present invention have a homozygous disruption in the RNase L gene of the their somatic cells and germ cells Such mutant mammals produce little to no RNase L and, therefore, are characterized as being RNase L null. The mutant mammals of the present invention comprise any non-human mammal. Such animals are, for example, rodents, non-human primates, sheep, dogs, cows, and pigs. The preferred non-human mammals are selected from the rodent family including rat and mouse, more preferably mouse.

The mutant non-human mammals of the present invention are produced by introducing a transgene into the germline of the non-human mammal. As used herein the "transgene" is a variant of the RNase L gene. The transgene comprises a disruption in the RNase L gene that normally is present in the non-human mammal, i.e., the wild-type or endogenous gene of the mammal. As used herein a "disruption" is a deletion of all or a portion of the RNase L gene or, preferably, an addition of a heterologous nucleic acid sequence to the RNase L gene. Preferably, the disruption is in a coding exon of the RNase L gene. In a preferred embodiment the disruption comprises the addition of a heterologous sequence between two nucleotides present in a region extending from about codon 23 to about codon 720, more preferably from about codon 56 to about codon 335 of the wild-type RNase L gene of the mammal.

Figure 9:
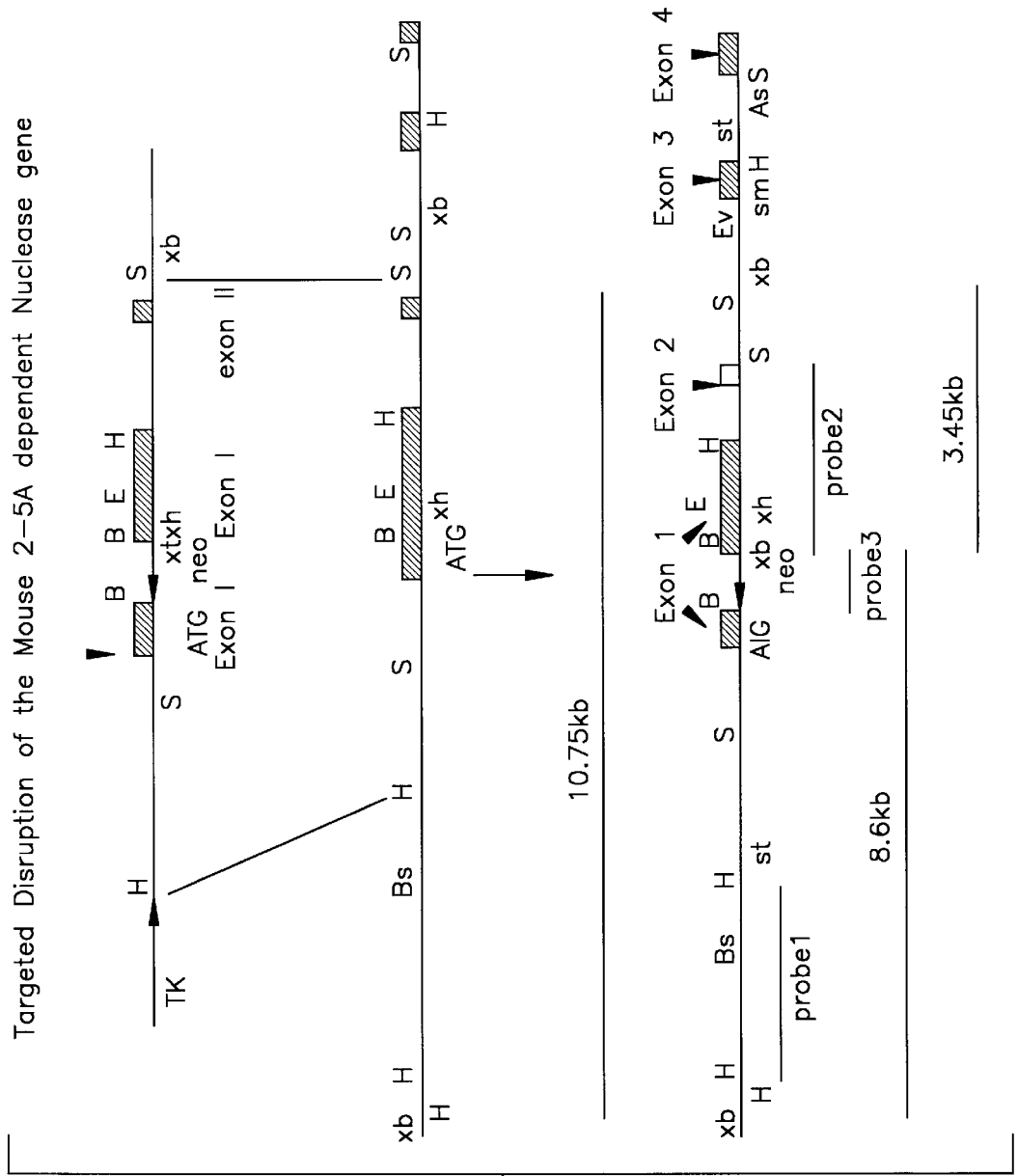
FIG. 9 is a schematic representation of the targeted disruption of the RNase L gene.
Figure 10:
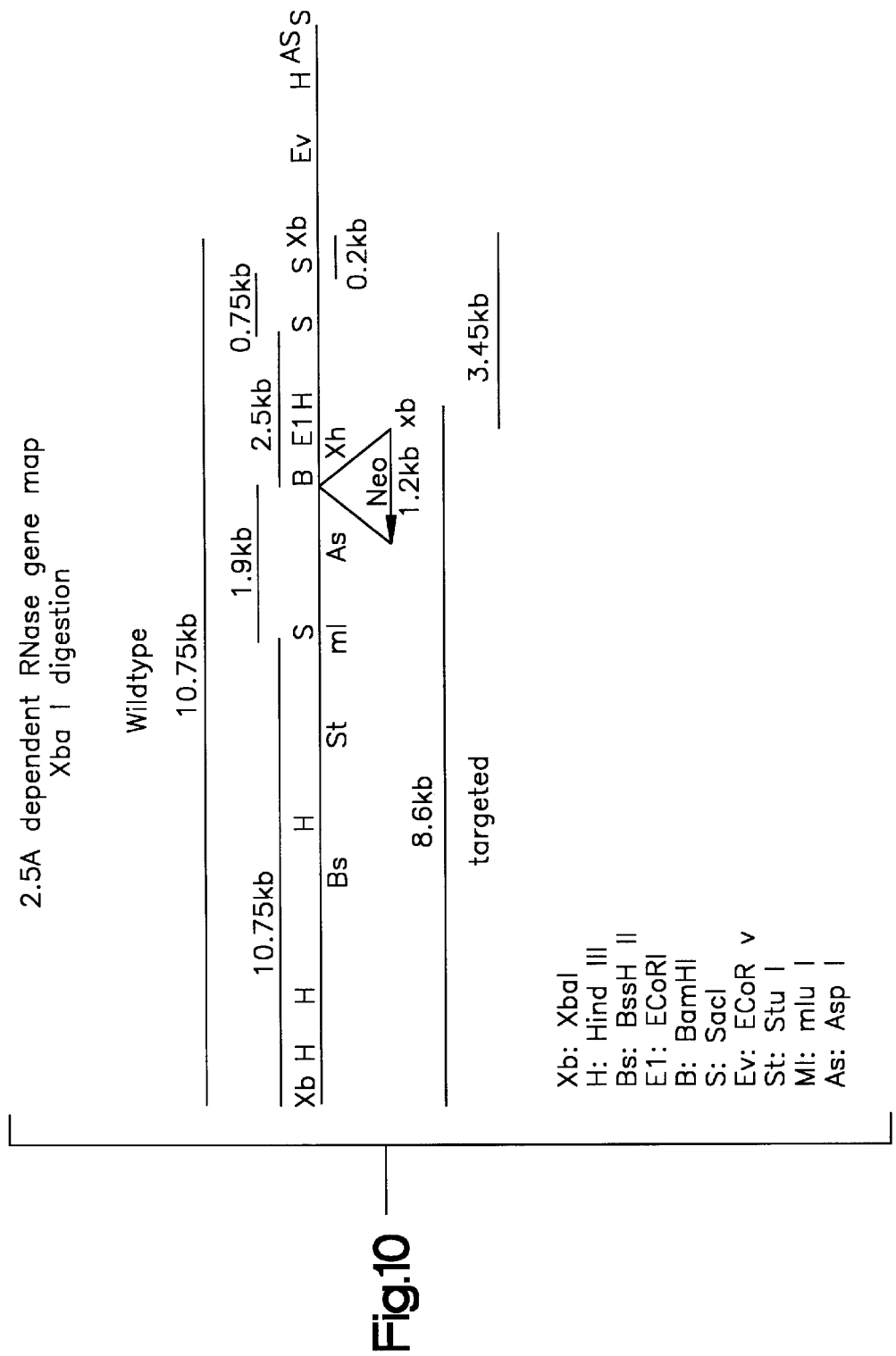
FIG. 10 shows a number of restriction enzyme sites in the mutant mouse RNase L gene and the size of the fragments produced when the mutant mouse RNase L gene is digested with these restriction enzymes.
Figure 11:
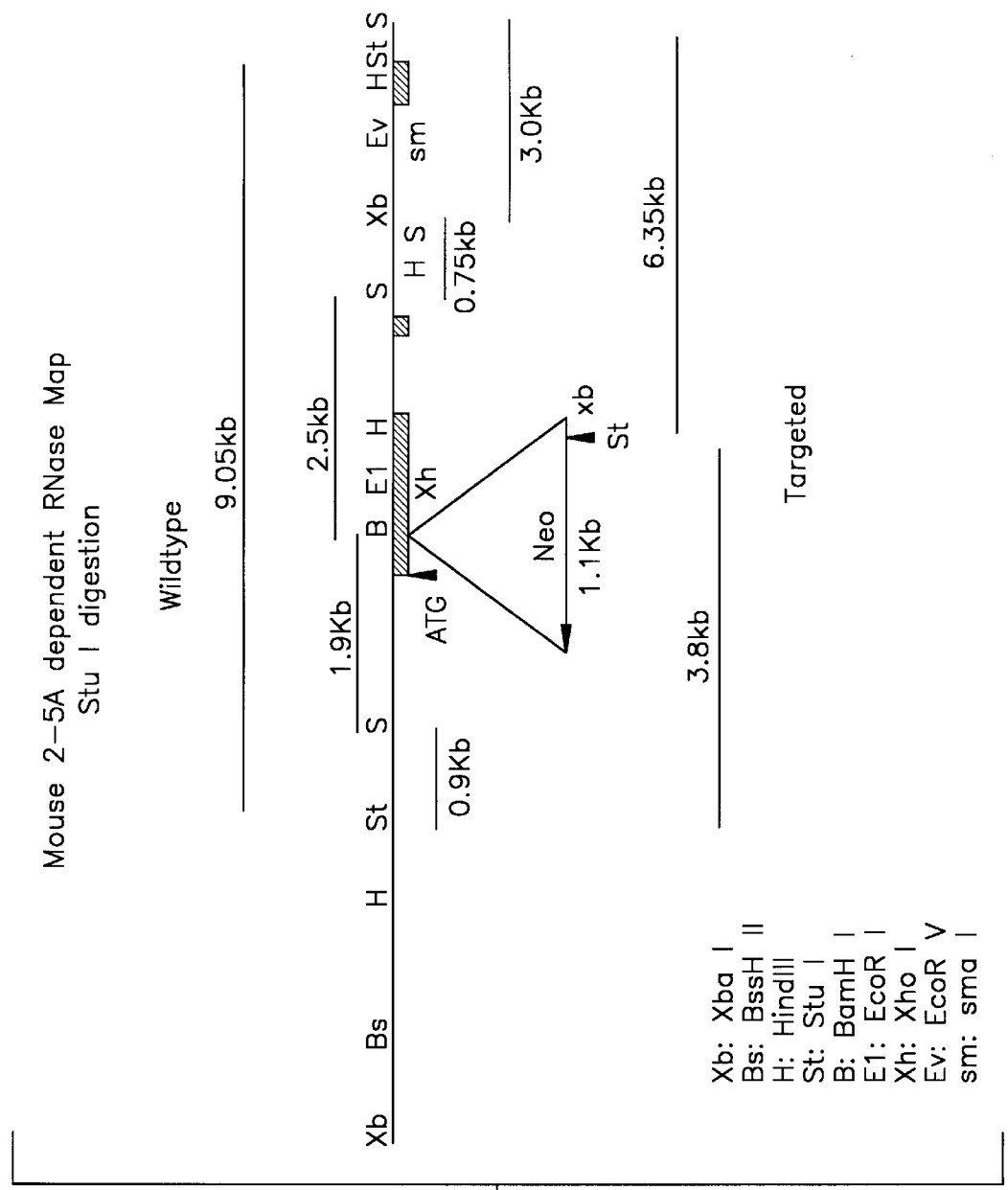
FIG. 11 shows a number of restriction enzyme sites in the mutant mouse RNase L gene and the size of the fragments produced when the mutant mouse RNase L gene is digested with these restriction enzymes.

In another aspect, the present invention relates to a DNA construct comprising a disrupted coding exon of an RNase L gene. As used herein a "disrupted coding exon" comprises a deletion of nucleic acid sequence from the wild-type sequence of the coding exon or an addition of a heterologous nucleic acid sequence to the wild-type sequence of the coding exon. Preferably, the DNA construct comprises a disrupted coding exon 1, coding exon 2, coding exon 3 or coding exon 4 of an RNase L gene, more preferably a disrupted coding exon 1, most preferably a disrupted coding exon 1 of the mouse RNase L gene. The nucleotide sequence of a cDNA which encodes mouse RNase L is shown in Table 2 and is set forth in SEQ. ID. NO. 3. The amino acid sequence of the mouse RNase L enzyme is shown in FIG. 9 and set forth in SEQ. ID. NO. 4. The first coding exon of the wild-type mouse RNase L gene encodes amino acids 1 to 491 and the second coding exon encodes amino acids 492–519. The third coding exon encodes amino acids 520 through 611.

Preferably, the heterologous nucleic acid sequence is a marker sequence. More preferably, the heterologous nucleic acid sequence comprises a marker sequence that is inserted in the reverse orientation as compared to the coding sequence of the RNase L gene. As used herein the term "marker sequence" refers to a nucleic acid sequence that is used (1) to disrupt expression of the RNase L gene and (2) to identify those cells that have incorporated the transgene into the genome thereof. Suitable marker sequences are those that encode an assayable or selectable product and include, for example, antibiotic resistance genes or genes that encode an assayable enzyme not typically found in the cell. Where the marker sequence encodes a protein, the marker sequence will also typically contain a promoter that regulates its expression. The methods for preparing such DNA constructs are well-known in the art and, typically, employ genomic libraries and standard recombinant techniques.

In another aspect the present invention relates to mutant, mammalian embryonic stem cells having a heterozygous or homozygous disruption in the RNase L gene thereof. Such mutant cells are made by introducing the transgene into the embryonic stem cells. Suitable embryonic stem cells are those that have the ability to integrate into and become part of the germ line of a developing embryo. Introduction of the transgene into the embryonic stem cell can be accomplished using a variety of methods well known in the art, such as for example, retrovirus-mediated transduction, microinjection, calcium phosphate treatment, or, preferably, electroporation. Thereafter, the transgene is integrated into the genome of some of the transfected cells, typically by non-homologous or homologous recombination. Screening for mutant cells is dependent on the type of disruption. If the transgene comprises an antibiotic resistance gene, the transfected cells are cultured in the presence of the antibiotic. If the transgene comprises a sequence encoding an assayable enzyme, the substrate for the enzyme can be added to the cells under suitable conditions, and the cells containing the product of enzymatic activity identified. If the transgene comprises a deletion in the RNase L gene sequence, i.e. a variant RNase L gene sequence, a Southern blot of the transfected cells genomic DNA can be probed with a sequence designed to hybridize with the variant sequence and to produce an additional, identifiable bond. The mutant cells containing the heterozygous or homozygous disruption in the RNase L gene are used to prepare the mutant animals of the present invention, typically by insertion into an embryo of the same species of animal.

Mutant non-human mammals comprising a homozygous disruption in the RNase L gene are useful for screening for drugs that induce transcription of RNase L or activate RNase L and, thus, produce antiviral and anticancer effects in wild-type mammal. The screening comprises the step of infecting the mutant mammals and wild-type mammals of the same species, for example wild-type mice and mutant mice comprising a homozygous disruption in the RNase L gene, with an infectious dose of a virus which is known to be susceptible to the 2-5A mediated antiviral effect of interferon, such as for example, ECMV. Varying doses of the drug are also injected into the wild-type mammals and the mutant mammals by conventional modes of injection, such as for example, by intravenous injection or intraperitoneal injection. The drug may be injected before or after infection with the virus. Control mammals are injected with carrier alone. The survivability of the mammals is monitored. In addition, several of the mammals from each group are sacrificed several days, such as for example 4 to 7 days, after treatment with the antiviral drug or carrier and the titer of the virus in several organs, such as for example liver, lung, spleen, kidney, and heart is determined. A finding that treatment with the antiviral drug inhibits production of virus in both the wild-type and the mutant animals indicates that the drug exerts its inhibitory effect through a mechanism that does not require a functional RNase L enzyme. In contrast, a finding that treatment with the antiviral drug inhibits production of virus in the wild type animals but not the mutant animals indicates that the antiviral effect of the drug is mediated by RNase L.

Mutant non-human mammals comprising a homozygous disruption in the RNase L gene thereof are also a source of cells, such as for example fibroblasts, that are useful for screening drugs that activate RNase L. Alternatively, heterozygous mammals comprising one disrupted RNase L gene and one wild type L gene can be used to produce such cells. Such heterozygous mammals are intercrossed and cells comprising a homozygous disruption in the RNase L gene thereof, such as for example fibroblasts are isolated from the resulting embryos. Thereafter, varying doses of the drug are added to the culture medium of the mutant cells and to the culture medium of wild-type cells from the same species. Control cultures receive carrier alone. The virus yields are then determined by viral plaque assays on indicator cells. A finding that treatment with the antiviral drug inhibits production of virus and cell death of both the wild-type and the mutant cells indicates that the drug does not exert its inhibitory effect by the 2-5A system. A finding that treatment with the antiviral drug inhibits production of virus in the wild type cultures but not the mutant cultures indicates that the antiviral effect of the drug is mediated by the 2-5A system.

The following examples are for purposes of illustration only and are not intended to limit the scope of the claims which are appended hereto.

EXAMPLE 1

A DNA Construct Comprising a Disrupted Coding Exon of the Mouse RNase L Gene

A. Characterization of the Wild-type RNase L Gene

Figure 1:
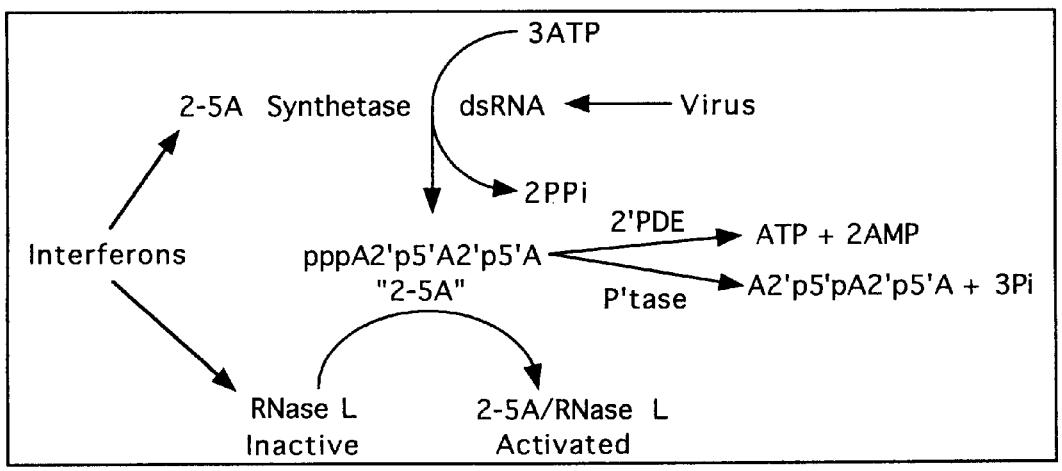
FIG. 1 is a schematic representation depicting the interaction of interferon and virus with the 2-5A system.

RNase L, which is found in basal levels in most mammalian cells is an unusual endoribonuclease that requires allosteric effectors to catalyze the hydrolysis of single-stranded RNA. The effectors which are needed to convert the inactive form of RNase L to the active form consist of a type of oligoadenylate called 2-5A with 2'-5' internucleotide linkages. It has been shown that treatment of mammalian cells with the antiviral agent interferon induces transcription not only of the RNase L gene but also of a set of genes encoding at least four different species of 2-5A synthetase. The newly-synthesized synthetases are then activated by binding to dsRNA, which is a frequent by-product of virus infection. Once stimulated, the 2-5A synthetases convert ATP to $PP_i$ and to a series of 2-5A molecules which then bind to the RNase L, thereby converting the RNase L from its inactive form to its catalytically active form. A schematic of the interactions between the components of the 2-5 A system, which includes RNase L, the 2-5A synthetases and the 2-5A effectors is shown in FIG. 1.

Figure 2:
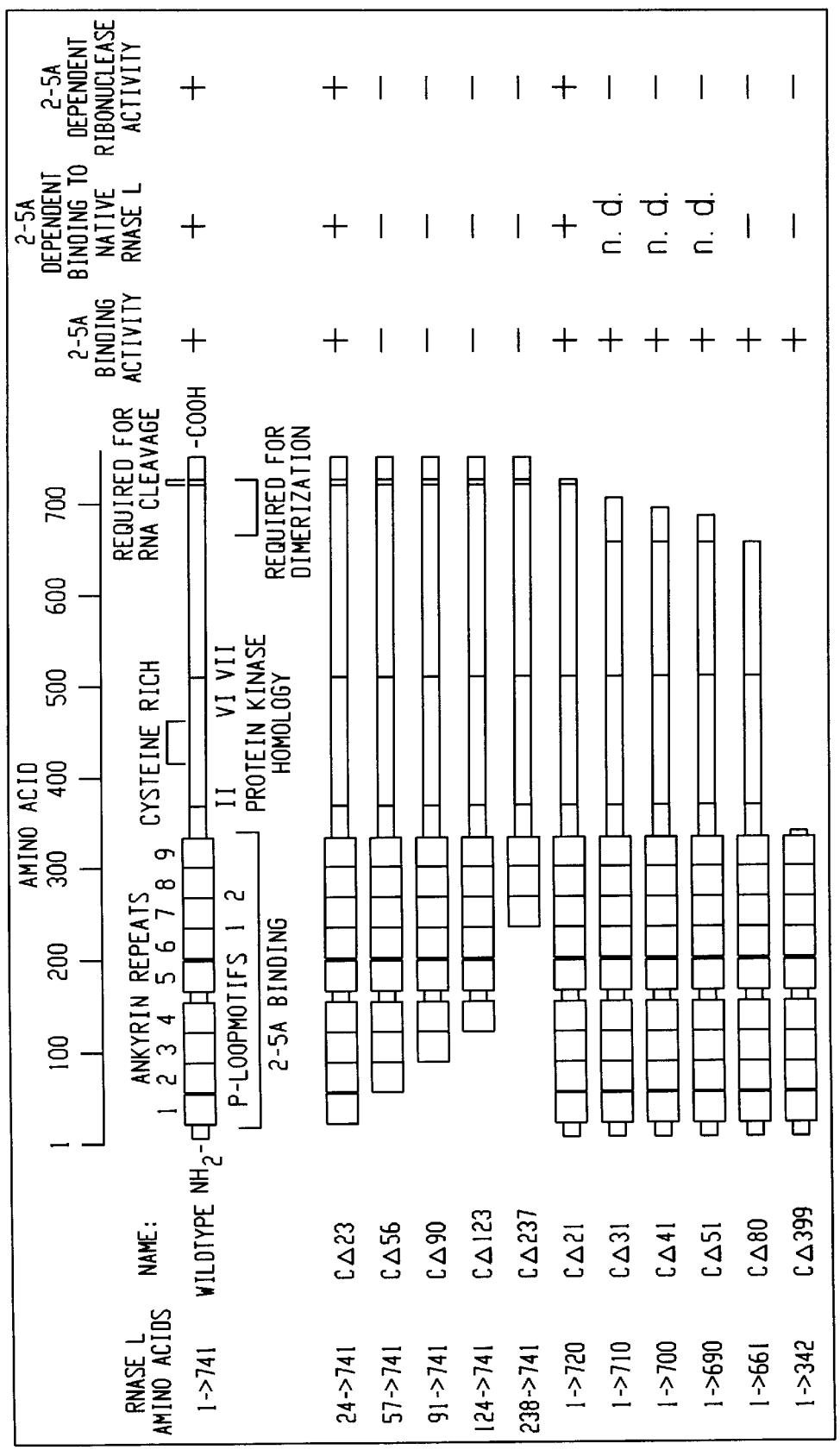
FIG. 2 is a schematic representation of the deletion mutants of RNase L and a description of the activities of the deletion mutants.

The affinity of RNase L for 2-5A (Kd=40 to 110 pM) is highly specific. As shown in FIG. 2, the amino terminal half of the enzyme comprises nine units of about 33 amino acids in length, each containing an ankyrin-related repeat sequence. Ankyrin repeats mediate interactions between and within many different proteins. These usually consist of 33 amino acid sequences of the general formula, -G-(T/S)(P/A)LHhAA--GH--h(V/A)--LL-GA--(D/N)----; where h is any hydrophobic amino acid. Ankyrins bind integral membrane proteins and tubulin through their N-terminal domains consisting of twenty-two such elements (Lux et al., 1990). A tripeptide sequence, GKT, implicated in 2-5A binding, appears twice in RNase L at positions 2 to 4 in the 7th and 8th ankyrin repeats, suggesting involvement of the ankyrin region in 2-5A dependent dimerization of RNase L. The GKT tripeptides are parts of a repeated phosphate-binding loop (P-loop) motif. Other interesting features of RNase L include a cysteine-rich region, a protein kinase homology region (to domains II, VI, and VII), and homology to *E. coli* RNase E. The C-terminal region of RNase L is required for RNase activity.

To precisely map the functional domains in RNase L, nested deletions of both termini of human RNase L cDNA were expressed as N-terminal glutathione S-transferase (GST) fusion proteins from vector pGEX-4T-3 (Pharmacia) in *E. coli*. The human RNase L cDNA was subcloned downstream of the coding sequence for GST in expression vector pGEX-4T-3 (Pharmacia). The nucleotide sequence of human RNase L cDNA, SEQ. ID. NO. 1, and the predicted amino acid sequence, SEQ. ID. NO. 2 of the human RNase L enzyme are shown in Table 1. The deletion mutants of RNase L, which are depicted in FIG. 2, were constructed by PCR and restriction enzyme cleavages. All mutants were confirmed by DNA sequence analysis. Induction in *E. coli* was at 30° C. with 0.1 mM IPTG for 5 h. To purify the fusion proteins, glutathione sepharose 4B (100 ml of a 50% slurry) was added to extract the protein from 50 ml of culture medium at room temperature for 30 min. After washing the protein-bead complexes three times with buffer, the fusion proteins were eluted with 20 mM of glutathione in 50 mM Tris-HCl, pH 8.0. Expression and purity of the protein preparations was determined by SDS/PAGE and coomassie blue staining and by probing Western blots with a monoclonal antibody to RNase L.

Following elution from the glutathione, the mutant RNase L fusion proteins were assayed for the ability to bind to a radioactive 2-5A analog in a filter binding assay according to Knight et al, (1980); Radioimmune, radiobinding and HPLC analysis of 2-5A and related oligonucleotides from intact cells; Nature 288: 189–192. 2-5A binding activity was determined with 3 μg of each of the fusion proteins by the filter binding method using a $^{32}$P-labeled and bromine substituted 2-5A analog, $p(A2'p)_2(br^8A2'p)_2A3'[^{32}P]pCp$ prepared according to Nolan-Sorden et al., (1990); Photochemical crosslinking in oligonucleotide-protein complexes between a bromine substituted 2-5A analogue and 2-5A-dependent RNase by ultraviolet lamp or laser; Anal. Biochem. 184: 298–304.

In addition, the 2-5A dependent RNase activity of the fusion proteins was assayed using $^{32}$P-labeled poly(rU) as a substrate as described in Dong et al. (1994) Intrinsic molecular activities of the interferon-induced 2-5A-dependent RNase, J. Biol. Chem. 269: 14153–14158. Incubations were in the presence or absence of 0.1 μM pA(2'p5'A)$_3$ at 30° C. for 30 min. RNA cleavage was determined in autoradiograms of sequencing gels. In addition, the ability of the fusion proteins to form stable heterodimers with the wild type, recombinant human RNase L from insect cells was determined.

Figure 3:
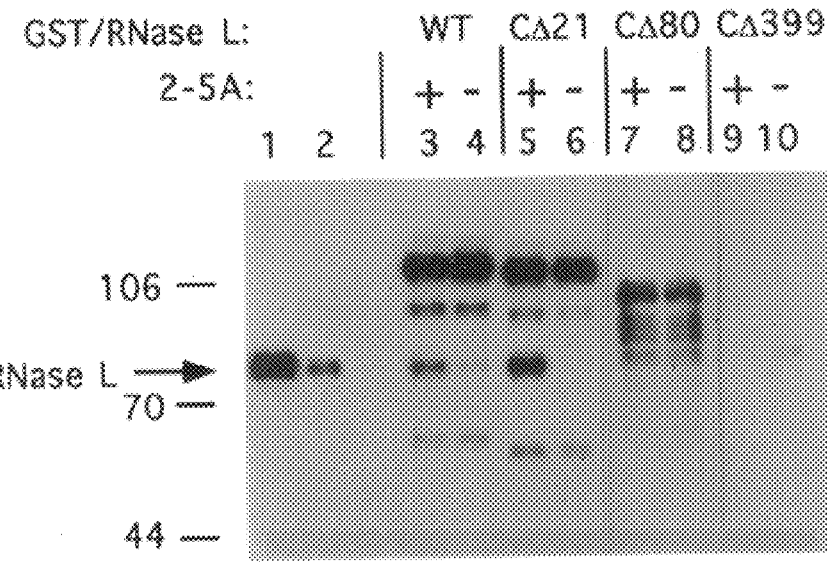
FIG. 3 is an autoradiogram which depicts the 2-5A dependent binding of the mutant RNase L fusion proteins to native human RNase L.
Figure 3:
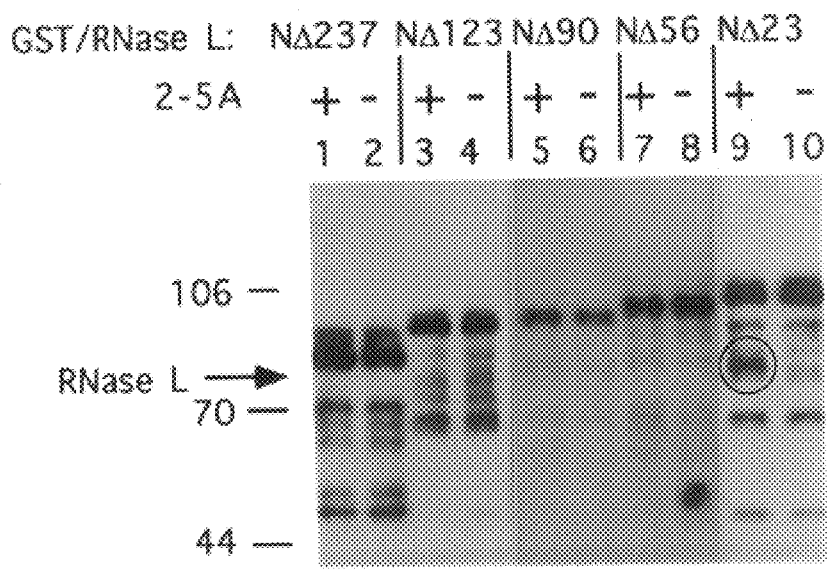

2-5A dependent binding of the mutant RNase L fusion proteins to native human RNase L (not a fusion protein) expressed in insect cells in the presence and absence of 2-5A was determined after immobilization on glutathione sepharose. This assay was performed by incubating 50 μg of extracts containing wild type or mutants of RNase L fused to GST with recombinant human RNase L (25 μg) from insect cells in the presence and absence of 0.8 μM pA(2'p5'A)$_3$ on ice for 2 h. Subsequently, glutathione sepharose was added and the mixture was incubated with shaking at room temperature for 20 min. Analysis of the bound protein was by SDS/PAGE and western blot analysis probed with antibody to RNase L using the enhanced chemiluminescence (ECL) method (Amersham). The results are shown in FIG. 3. In FIG. 3, lanes 1 and 2 contain 1 μg and 0.15 μg of insect cell extract containing human recombinant RNase L. RNase L is indicated by the arrows and by the circle in panel B, lane 9.

As shown in FIG. 3, none of the proteins had ribonuclease activity or RNase L-binding activity when incubated in the absence of 2-5A. Deletion of only the N-terminal 23 amino acids or the C-terminal 21 amino acids had no effect on any of the activities of RNase L (FIG. 3). However, further deletions from the N-terminus caused a loss of 2-5A binding, 2-5A-dependent RNase, and 2-5A-dependent dimerization activities (see mutant NΔ56 containing an N terminal deletion of 56 residues). Deletion of 31 amino acids from the C-terminus caused a loss in 2-5A dependent ribonuclease activity while retaining 2-5A binding activity (mutant CΔ31). Thus, amino acid residues 710 to 720 are necessary for 2-5A-dependent RNase activity. The 2-5A binding activity is clearly localized in the N-terminal half of the RNase L. For example, mutant CΔ399 which lacks the C-terminal 399 residues of RNase L still binds 2-5A as well as the complete wild type enzyme.

Of the proteins analyzed, only the GST/wild type RNase L, and the GST/CΔ21 and GST/NΔ23 RNase L mutants bound native RNase L in the presence of 2-5A. The antibody recognized an epitope in the N-terminal half of RNase L and therefore the CΔ399 mutant could not be seen on the western blot; however the protein was clearly visualized by staining the protein in the gel with coomassie blue dye (not shown). In summary, 2-5A binding requires amino acid residues 23–342, 2-5A-dependent ribonuclease activity apparently requires the sequence EYRKHFPQTH (residues 711 to 720), and 2-5A-dependent dimerization requires the 2-5A binding domain as well as C-terminal sequence between residues 661 and 720 (FIGS. 2 and 3).

Figure 4:
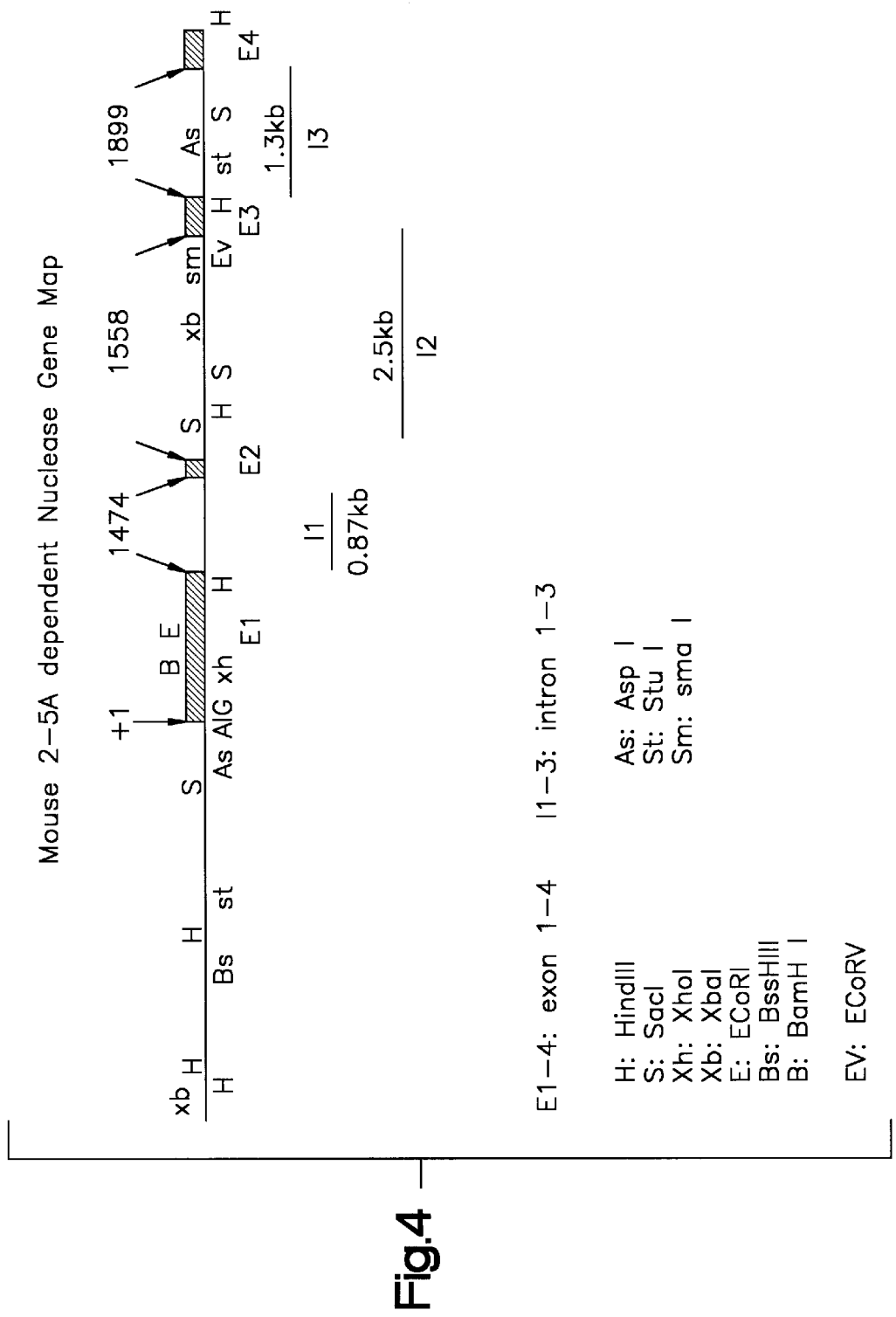
FIG. 4 shows the mouse RNase L gene map.
Figure 5:
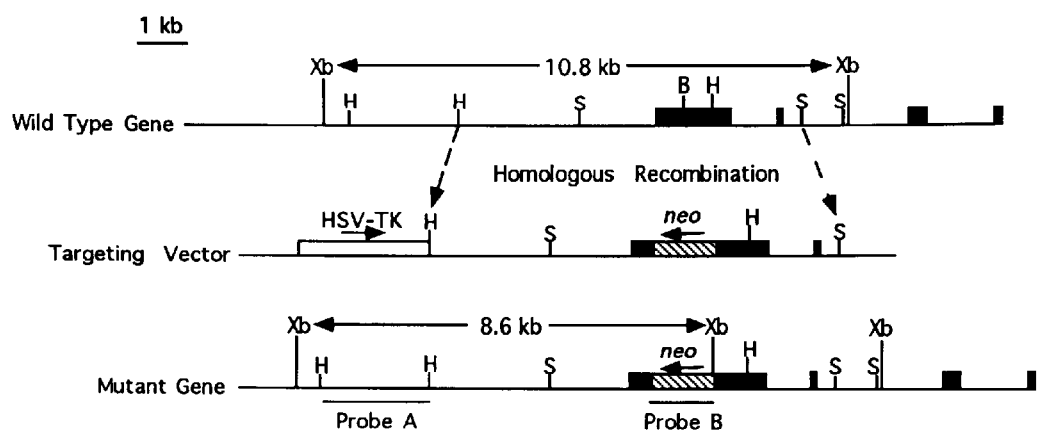
FIG. 5 is a schematic representation of the mouse wild-type RNase L gene, a portion of the targeting vector used to produce a mutant mouse having a homozyogous disruption in the RNase L gene thereof; and the mutant gene produced by homologous recombination of the wild-type gene and the targeting vector.
Figure 8:
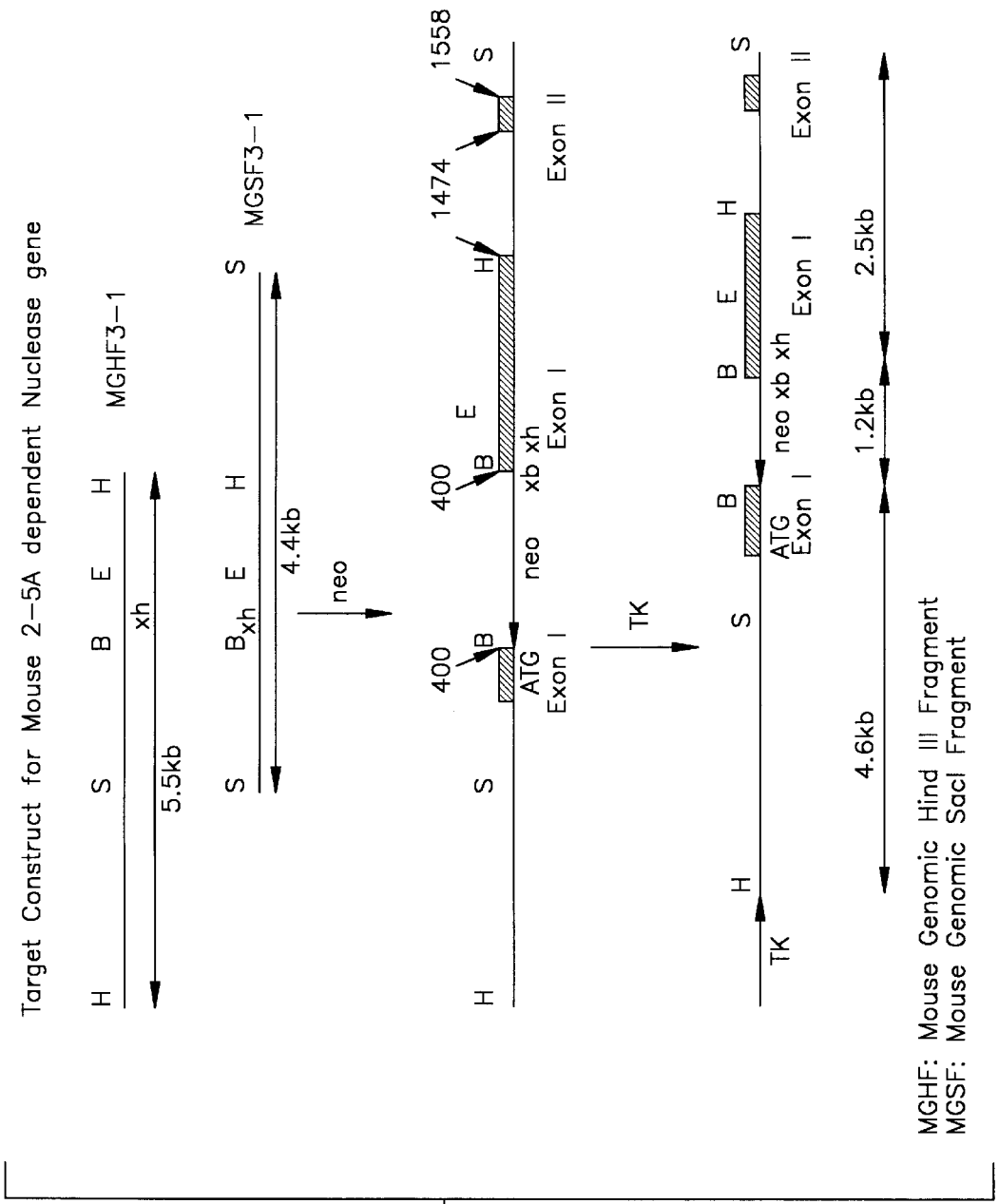
FIG. 8 shows a restriction enzyme map of clones MGHF3-1 and MGSF3-1 and the steps involved in producing the targeting vector.

B. A DNA Construct Comprising a Disrupted Coding Exon 1 of the Mouse RNase L Gene A targeting vector containing a disrupted coding exon 1 of the mouse RNase L gene, a portion of the mouse RNase L gene sequence upstream of the first coding exon, the second coding exon of the mouse RNase L gene, and the neomycin resistance gene (neo) incorporated into the sequence of the coding exon 1, was prepared employing standard recombinant techniques Kpn I. The neo insertion was in codon number 100 of the RNase L gene. In addition, an HSV thymidine kinase gene was linked to the 5' terminus of the RNase L gene fragments. A schematic representation of the targeting vector is shown in FIG. 5. The exons are indicated by black boxes. The direction of the RNase L gene transcription is from left to right. The general scheme of preparing the targeting vector is depicted in FIG. 8. The gene map of the mouse RNase L gene is shown in FIG. 4. To prepare the targeting vector two overlapping genomic subclones for mutant RNase L were isolated from a lambda dash phage library of mouse strain 129 DNA (provided by T. Doetschman, University of Cincinnati) by screening with a $^{32}$P-labeled murine RNase L cDNA probe. Such libraries are also available from commercial sources, such as for example Genome Systems Inc. of St. Louis Mo. As shown in FIG. 8, the Hind III fragment from one subclone, designated MGHF3-1 fragments, and the SacI fragment from the other subclone, designated MGSF3-1, were used to prepare the construct. Clone MGHF3-1 contains the 3' end of coding exon 1 and all of exon 2. Each of the fragments were digested with BamHl and a neo gene isolated from plasmid pmclneopolyA, obtained from Stratagene, was inserted in reverse orientation into a BamHl site in the first coding exon of the RNase L gene. Thereafter, a herpes simplex virus thymidine kinase (TK) gene was fused to the 5' end of the gene fragment (FIG. 8).

EXAMPLE 2

Mouse Embryonic Stem Cells Comprising a Heterozygous Disruption in the RNase L Gene Thereof Embryonic cells (ES) from mouse strain 129/O1a were cultured on mef/IC feeder layers of embryonic fibroblasts, obtained from T. Doetschman, University of Cincinnati. The MEF feeder cells were treated with 10 μg per ml mitomycin C in Dulbecco's modified Eagle's medium supplemented with 15% fetal bovine serum and 0.1 mM 2-mercaptoethanol, and 1000 units/ml leukemia inhibitory factor. 50 ug of the KpnI linearized targeting vector was electroporated into 8×10$^7$ ES cells in 1 ml of ES medium at 160V/200 uF in Gibco-BRL Cellporator. Cells were plated on feeder layers in ten 100 mm dishes and refed the next day and every subsequent second day with ES DMEM containing 200 ug/ml G418(active)(Gibco BRL) and 650 ng/ml ganciclovir (CCF, pharmacy). Drug-resistant clones were picked up 8–10 days later and propagated in 48 well plates in ES medium containing 250 ug/ml G418 and then each clone population was divided into two parts. One half was for storage and the other half was used for making DNA. Genomic DNA of each clone was isolated and digested with XbaI, resolved by electrophoresis through 1% agarose gel, and transferred to nytran plus membrane. The blots were hybridized to two $^{32}$P-labeled DNA probes in PBS-SDS hybridization buffer at 65° C. The $^{32}$P-labeled DNA probes included one probe from the murine RNase L gene outside of the sequence contained in the DNA construct (Probe A), i.e., PROBE A was designed to hybridize with an RNase L gene sequence which is upstream from the sequence fused to the TK gene, as shown in FIG. 5. The second $^{32}$P-labeled probe was designed to hybridize to the neo gene (Probe B).

Figure 6:
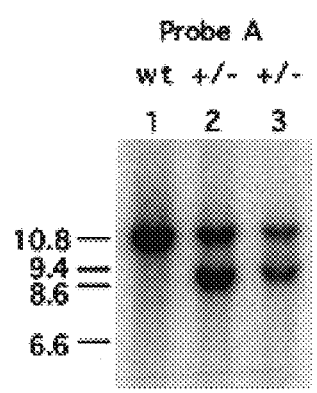
FIG. 6 depicts the Southern (DNA) blot analysis of Xbal-digested genomic DNA from wild-type and mutant ES cells hybridized to Hindlll DNA probe "A" or to a neo DNA probe "B".
Figure 6:
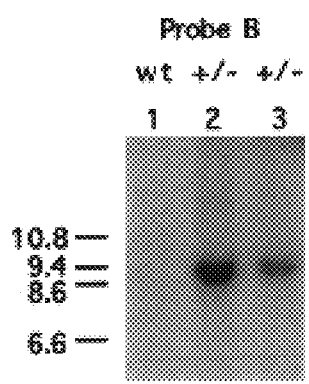

The results of Southern (DNA) blot analysis of XbaI-digested genomic DNA from the ES cells are shown in panel B and panel C of FIG. 6. The sizes indicated are in kilobases. The parental ES cell DNA (lane 1) containing only the wild type RNase L gene produced the expected 10.8 kb fragment which hybridized to a Hind III DNA probe A (FIG. 6B). In contrast, after screening about 250 drug resistant clones, two ES cell lines with a homologous recombination of the RNase L gene were obtained (FIGS. 6B and C, lanes 2 and 3). The DNA from these cells digested with XbaI produced an additional band of 8.6 kb which hybridized both to the RNase L genomic probe "A" and to the neo DNA probe "B". These ES cell lines, AZ3 and AZ16, are thus heterozygous for the wild type RNase L gene. Karyotype analysis on these cell showed that they contained a diploid number of chromosomes. The ES cell line AZ16 was deposited with the American Type Culture Collection (ATCC), 12301 Parklawn Drive, Rockville, Md., on Sep. 30, 1997 and was given Accession Number ATCC CRL-12406.

EXAMPLE 3

A Mutant Mice Comprising a Homozygous Disruption in the RNase L Gene Thereof

ES cells containing the target construct in the proper location in the genome were then inserted into an embryo and implanted into the uterus of a pseudopregnant foster mothers. In the preferred embodiment, the recombinant ES cells, AZ16, were injected into blastocyst mouse embryos and implanted into foster mothers. These mice were grown, bred, and the offspring characterized to determine germ line transmissibility. The DNA from tail clippings of these offspring were analyzed in Southern blots to confirm germ line transmission of the disrupted RNase L gene, i.e the transgene. The genotypes were determined by southern blot analysis of XbaI-digested genomic DNA hybridized to $^{32}$P-labeled genomic RNase L DNA probe "A" (see FIG. 6.0). This DNA probe lies outside the targeting vector and clearly differentiates between the wild type and the disrupted RNase L gene. After establishing germ line transmissions, the heterozygote mice were crossed and RNase L$^{-/-}$ mice were obtained.

Figure 7:
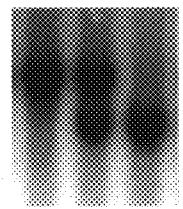
FIG. 7 (upper panel) shows the Southern (DNA) blot analysis of DNA extracted from wild-type and mutant mice having a homozygous disruption in the RNase L gene.
Figure 7:
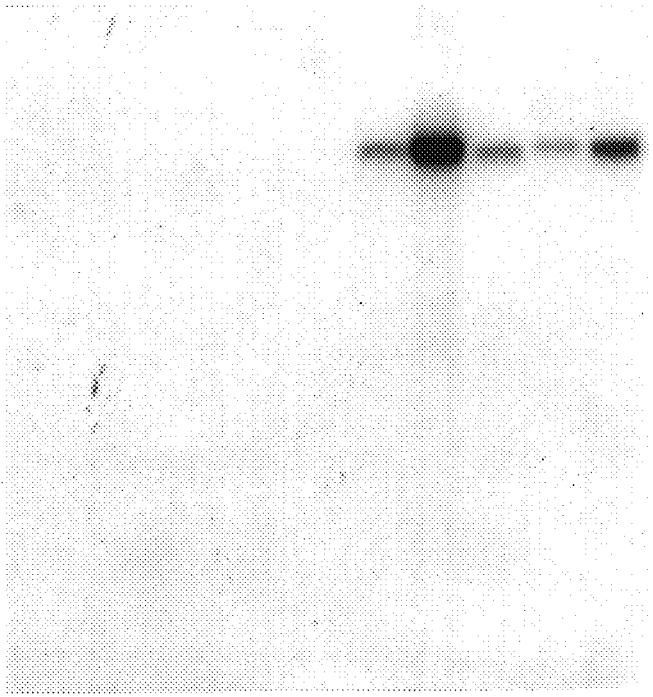

To establish the absence of the wild type RNase L gene in the mutant mice, DNA isolated from tails of normal and mutant mice and used to determine the genotypes of the mice by Southern blot analysis (FIG. 7, upper panel). As shown in lane 3, mice lacking the wild type RNase L gene were obtained.

To further monitor RNase L in the mice, extracts of several different organs were incubated with a high specific activity, $^{32}$P-labeled and bromine-substituted 2-5A analog, $_p$(A2'p)$_2$(br$^8$A2'p)$_2$A[$^{32}P$]Cp (Nolan-Sorden et al., Anal. Biochem. 184: 298–304, 1990). Upon irradiation with UV light at 308 nm, the 2-5A analog was covalently crosslinked to RNase L in extracts of seven different organs of the wild type mice. After crosslinking and electrophoresis of SDS/polyacrylamide gels, the labeled RNase L was visualized on autoradiograms of gel. The highest levels of RNase L were found in the spleen, thymus, lung and testis with lesser amounts in the kidney, liver and heart of the wild-type mice. In contrast, no RNase L or 2-5A binding proteins were found in extracts of organs of the RNase L$^{-/-}$ mice. Thus the RNase L$^{-/-}$ mice are shown to be completely lacking in RNase L.

EXAMPLE 4

Mutant Mouse Cells Containing a Homozygous Disruption in the RNase L Gene

Cells containing a homozygous disruption in the RNase L gene thereof were obtained by intercrossing mice containing a heterozygous disruption in the RNase L gene and isolating mouse embryo fibroblasts (MEFs) from the resulting embryos at day 16.5 post-coitum. Individual sibling embryos were removed, while maintaining sterility, to tissue culture dishes containing PBS. The embryos were minced and pieces of tissue were removed for genotyping by Southern blot analysis. The remaining tissue was incubated at 4° C. for 16 h with 0.05% trypsin and 0.53 mM EDTA. The excess trypsin solution was then aspirated and discarded and the tissue was incubated at 37° C. for 30 min. Two volumes of DMEM containing 10% FBS was added followed by vigorous pipetting to break up the tissue into cells. The cells were then cultured in fresh DMEM/10% FBS. Cell lines were derived by continuous culturing for 10 to 14 passages to obtain immortalized mutant cells.

Wild-type mouse embryo fibroblasts and mutant mouse embryo fibroblasts comprising the homozygous disruption in the RNase L gene were pretreated for 16 h with 1,000 units per ml of interferon α to enhance levels of RNase L in the wild type cells. RNase L was clearly detected in the wild type cells and was enhanced by interferon treatment of the cells. In contrast, RNase L could not be detected in the RNase L$^{-/-}$ MEF cells regardless of the presence or absence of interferon treatment of the cells.

B. Using the Mutant Mice and Mutant Cells to Determine the Mechanism by which Interferon Exerts an Anti-Viral Effect in Mammals Wild type and RNase L$^{-/-}$ MEF cell lines were preincubated in the absence or presence interferon α. The cells were also infected with EMCV at an multiplicity of infection (M.O.I.) of 0.01 plaque forming units (p.f.u.) per cell and incubated for two viral replication cycles (14 h). The interferon treatments resulted in dose-dependent decreases in viral yields in both the wild type and RNase L$^{-/-}$ cells. However, with 0, 100 or 10,000 units per ml of added interferon there were 4-, 6- and 8-fold higher levels of virus produced in RNase L$^{-/-}$ cells compared to wild type cells. At a higher M.O.I. (0.1), the differences between the cell lines was reduced. These findings show that cells containing a homozygous disruption in the RNase L gene thereof are useful for characterizing the involvement of the 2-5A system in mediating the antiviral effect of an antiviral agent, such as interferon.

Wild-type mice and mutant mice comprising a homozygous disruption in the RNase L gene were treated with interferon α. One day after treatment, both groups of mice were injected intraperiotoneally (i.p.) with 100 p.f.u. of EMCV. The survival of the mice with and without treatment with interferon α was determined. Even in the absence of interferon treatment, the RNase L$^{-/-}$ mice succumbed to infection before the viral-infected wild type mice. The times, postinfection, required for about half of the mice to die were 5.5 d and 8.5 d for the RNase L$^{-/-}$ and wild type mice, respectively. Effects of interferon α (10$^4$ units), delivered i.p. one day prior to infection, were determined. The times, postinfection, for about half of the interferon-treated animals to die were 10.5 d and 15.5 d for the RNase L$^{-/-}$ mice and wild type mice, respectively. Therefore, interferon-treatment delayed death by about 5 d and 7 d in the RNase L$^{-/-}$ and wild type mice, respectively. These results show that RNase L contributes to the antiviral mechanism of interferon action in mice. These results also show that the RNase L$^{-/-}$ mice are useful for determining the involvement of the 2-5A system in mediating the antiviral effect of an antiviral drug.

What is claimed is:

1. A mouse whose genome comprises a homozygous disruption of exon 1 of the RNase L gene, wherein the disruption comprises an addition of a heterologous sequence into exon 1 or a deletion of a portion of exon 1; wherein said mouse is RNase L$^{-/-}$; and wherein said mouse further has a reduced response to interferon-alpha treatment following encephalomyocarditis viral infection as compared to a wild-type mouse.

2. The mouse of claim 1, wherein the disruption is an addition of a heterologous sequence into exon 1.

3. The mouse of claim 2 wherein the heterologous sequence is a marker sequence.

4. The mouse of claim 3 wherein the marker sequence is between two nucleotides located in a region of exon 1 extending from codon 23 to codon 491.

5. The mouse of claim 1 wherein said mouse lacks functional RNase L enzyme.

6. A DNA construct comprising a partial or full sequence of a coding exon of a mammalian RNase L gene, said coding exon having a disruption therein.

7. An isolated mouse embryonic stem cell whose genome comprises a wild-type mouse RNase L allele and a disrupted mouse RNase L allele, said disrupted mouse RNase L allele comprising an addition of a heterologous sequence to the first exon of the disrupted mouse RNase L allele.

8. The mouse embryonic stem cell of claim 7 wherein the heterologous sequence is a marker sequence.

9. The mouse embryonic stem cell of claim 7 wherein said stem cell is a mouse stem cell having the ATCC Accession Number CRL-12406.

10. An isolated mouse cell whose genome comprises a homozygous disruption in exon 1 of the RNase L gene, wherein the disruption is an addition of a heterologous sequence into exon 1 or a deletion of a portion of exon 1, and wherein said mouse cell lacks functional RNase L enzyme.

11. The mouse cell of claim 10 wherein the homozygous disruption is an addition of a heterologous sequence to exon 1 of the mouse RNase L gene.

12. The mouse cell of claim 10 wherein said mouse cell is isolated from the mouse of claim 1.

13. The mouse cell of claim 11 wherein the heterologous sequence is a marker sequence.

14. The mouse cell of claim 13 wherein the marker sequence is disposed between codon 56 and codon 335.

* * * * *

UNITED STATES PATENT AND TRADEMARK OFFICE
CERTIFICATE OF CORRECTION

PATENT NO. : 6,028,243
DATED : February 22, 2000
INVENTOR(S) : Robert H. Silverman and Aimin Zhou It is certified that error appears in the above-identified patent and that said Letters Patent is hereby corrected as shown below:

Col. 3, line 38, delete "table 2" and insert -- Fig. 13 --.

Col. 3, line 40, delete "Fig. 9" and insert -- Fig. 13 --.

Col. 6, line 3, delete "table 1" and insert -- Fig. 12 --.

Col. 7, line 31, after "techniques" delete "Kpnl".

Col. 29, line 13, after "A DNA construct comprising" delete "a partial or full sequence of a coding exon of a mammalian RNase L gene, said coding exon having a disruption therein" and insert -- the mouse RNase L gene and a marker sequence, said marker sequence being disposed within exon 1 of the RNase L gene --.

Signed and Sealed this

Ninth Day of January, 2001

*Attest:*

Q. TODD DICKINSON

*Attesting Officer*    *Commissioner of Patents and Trademarks*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2931 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 104..2326

(xi) SEQUENCE DESCRIPTION: SEQ ID NO:1:

```
AATCCCAACT TACACTCAAA GCTTCTTTGA TTAAGTGCTA GGAGATAAAT TTGCATTTTC        60

TCAAGGAAAA GGCTAAAAGT GGTAGCAGGT GGCATTTACC GTC ATG GAG AGC AGG        115
                                                 Met Glu Ser Arg
                                                  1

GAT CAT AAC AAC CCC CAG GAG GGA CCC ACG TCC TCC AGC GGT AGA AGG        163
Asp His Asn Asn Pro Gln Glu Gly Pro Thr Ser Ser Ser Gly Arg Arg
 5              10                  15                  20

GCT GCA GTG GAA GAC AAT CAC TTG CTG ATT AAA GCT GTT CAA AAC GAA        211
Ala Ala Val Glu Asp Asn His Leu Leu Ile Lys Ala Val Gln Asn Glu
                25                  30                  35

GAT GTT GAC CTG GTC CAG CAA TTG CTG GAA GGT GGA GCC AAT GTT AAT        259
Asp Val Asp Leu Val Gln Gln Leu Leu Glu Gly Gly Ala Asn Val Asn
            40                  45                  50

TTC CAG GAA GAG GAA GGG GGC TGG ACA CCT CTG CAT AAC GCA GCA GTA        307
Phe Gln Glu Glu Glu Gly Gly Trp Thr Pro Leu His Asn Ala Ala Val
        55                  60                  65

CAA ATG AGC AGG GAG GAC ATT GTG GAA CTT CTG CTT CGT CAT GGT GCT        355
Gln Met Ser Arg Glu Asp Ile Val Glu Leu Leu Leu Arg His Gly Ala
    70                  75                  80

GAC CCT GTT CTG AGG AAG AAG AAT GGG GCC ACG CTT TTT ATC CTC GCA        403
Asp Pro Val Leu Arg Lys Lys Asn Gly Ala Thr Leu Phe Ile Leu Ala
85                  90                  95                 100

GCG ATT GCG GGG AGC GTG AAG CTG CTG AAA CTT TTC CTT TCT AAA GGA        451
Ala Ile Ala Gly Ser Val Lys Leu Leu Lys Leu Phe Leu Ser Lys Gly
                105                 110                 115

GCA GAT GTC AAT GAG TGT GAT TTT TAT GGC TTC ACA GCC TTC ATG GAA        499
Ala Asp Val Asn Glu Cys Asp Phe Tyr Gly Phe Thr Ala Phe Met Glu
            120                 125                 130

GCC GCT GTG TAT GGT AAG GTC AAA GCC CTA AAA TTC CTT TAT AAG AGA        547
Ala Ala Val Tyr Gly Lys Val Lys Ala Leu Lys Phe Leu Tyr Lys Arg
        135                 140                 145

GGA GCA AAT GTG AAT TTG AGG CGA AAG ACA AAG GAG GAT CAA GAG CGG        595
Gly Ala Asn Val Asn Leu Arg Arg Lys Thr Lys Glu Asp Gln Glu Arg
    150                 155                 160

CTG AGG AAA GGA GGG GCC ACA GCT CTC ATG GAC GCT GCT GAA AAA GGA        643
Leu Arg Lys Gly Gly Ala Thr Ala Leu Met Asp Ala Ala Glu Lys Gly
165                 170                 175                 180

CAC GTA GAG GTC TTG AAG ATT CTC CTT GAT GAG ATG GGG GCA GAT GTA        691
His Val Glu Val Leu Lys Ile Leu Leu Asp Glu Met Gly Ala Asp Val
                185                 190                 195

AAC GCC TGT GAC AAT ATG GGC AGA AAT GCC TTG ATC CAT GCT CTC CTG        739
Asn Ala Cys Asp Asn Met Gly Arg Asn Ala Leu Ile His Ala Leu Leu
            200                 205                 210

AGC TCT GAC GAT AGT GAT GTG GAG GCT ATT ACG CAT CTG CTG CTG GAC        787
Ser Ser Asp Asp Ser Asp Val Glu Ala Ile Thr His Leu Leu Leu Asp
        215                 220                 225

CAT GGG GCT GAT GTC AAT GTG AGG GGA GAA AGA GGG AAG ACT CCC CTG        835
His Gly Ala Asp Val Asn Val Arg Gly Glu Arg Gly Lys Thr Pro Leu
    230                 235                 240

ATC CTG GCA GTG GAG AAG AAG CAC TTG GGT TTG GTG CAG AGG CTT CTG        883
Ile Leu Ala Val Glu Lys Lys His Leu Gly Leu Val Gln Arg Leu Leu
245                 250                 255                 260

GAG CAA GAG CAC ATA GAG ATT AAT GAC ACA GAC AGT GAT GGC AAA ACA        931
Glu Gln Glu His Ile Glu Ile Asn Asp Thr Asp Ser Asp Gly Lys Thr
                265                 270                 275
```

```
GCA CTG CTG CTT GCT GTT GAA CTC AAA CTG AAG AAA ATC GCC GAG TTG      979
Ala Leu Leu Leu Ala Val Glu Leu Lys Leu Lys Lys Ile Ala Glu Leu
            280                 285                 290

CTG TGC AAA CGT GGA GCC AGT ACA GAT TGT GGG GAT CTT GTT ATG ACA     1027
Leu Cys Lys Arg Gly Ala Ser Thr Asp Cys Gly Asp Leu Val Met Thr
        295                 300                 305

GCG AGG CGG AAT TAT GAC CAT TCC CTT GTG AAG GTT CTT CTC TCT CAT     1075
Ala Arg Arg Asn Tyr Asp His Ser Leu Val Lys Val Leu Leu Ser His
    310                 315                 320

GGA GCC AAA GAA GAT TTT CAC CCT CCT GCT GAA GAC TGG AAG CCT CAG     1123
Gly Ala Lys Glu Asp Phe His Pro Pro Ala Glu Asp Trp Lys Pro Gln
325                 330                 335                 340

AGC TCA CAC TGG GGG GCA GCC CTG AAG GAT CTC CAC AGA ATA TAC CGC     1171
Ser Ser His Trp Gly Ala Ala Leu Lys Asp Leu His Arg Ile Tyr Arg
            345                 350                 355

CCT ATG ATT GGC AAA CTC AAG TTC TTT ATT GAT GAA AAA TAC AAA ATT     1219
Pro Met Ile Gly Lys Leu Lys Phe Phe Ile Asp Glu Lys Tyr Lys Ile
        360                 365                 370

GCT GAT ACT TCA GAA GGA GGC ATC TAC CTG GGG TTC TAT GAG AAG CAA     1267
Ala Asp Thr Ser Glu Gly Gly Ile Tyr Leu Gly Phe Tyr Glu Lys Gln
    375                 380                 385

GAA GTA GCT GTG AAG ACG TTC TGT GAG GGC AGC CCA CGT GCA CAG CGG     1315
Glu Val Ala Val Lys Thr Phe Cys Glu Gly Ser Pro Arg Ala Gln Arg
390                 395                 400

GAA GTC TCT TGT CTG CAA AGC AGC CGA GAG AAC AGT CAC TTG GTG ACA     1363
Glu Val Ser Cys Leu Gln Ser Ser Arg Glu Asn Ser His Leu Val Thr
405                 410                 415                 420

TTC TAT GGG AGT GAG AGC CAC AGG GGC CAC TTG TTT GTG TGT GTC ACC     1411
Phe Tyr Gly Ser Glu Ser His Arg Gly His Leu Phe Val Cys Val Thr
            425                 430                 435

CTC TGT GAG CAG ACT CTG GAA GCG TGT TTG GAT GTG CAC AGA GGG GAA     1459
Leu Cys Glu Gln Thr Leu Glu Ala Cys Leu Asp Val His Arg Gly Glu
        440                 445                 450

GAT GTG GAA AAT GAG GAA GAT GAA TTT TCC CGA AAT GTC CTG TCA TCT     1507
Asp Val Glu Asn Glu Glu Asp Glu Phe Ser Arg Asn Val Leu Ser Ser
    455                 460                 465

ATA TTT AAG GCT GTT CAA GAA CTA CAC TGG TCC TGT GGA TAC ACC CAC     1555
Ile Phe Lys Ala Val Gln Glu Leu His Trp Ser Cys Gly Tyr Thr His
470                 475                 480

CAG GAT CTG CAA CCA CAA AAC ATC TTA ATA GAT TCT AAG AAA GCT GCT     1603
Gln Asp Leu Gln Pro Gln Asn Ile Leu Ile Asp Ser Lys Lys Ala Ala
485                 490                 495                 500

CAC CTG GCA GAT TTT GAT AAG AGC ATC AAG TGG GCT GGA GAT CCA CAG     1651
His Leu Ala Asp Phe Asp Lys Ser Ile Lys Trp Ala Gly Asp Pro Gln
            505                 510                 515

GAA GTC AAG AGA GAT CTA GAG GAC CTT GGA CGG CTG GTC CTC TAT GTG     1699
Glu Val Lys Arg Asp Leu Glu Asp Leu Gly Arg Leu Val Leu Tyr Val
        520                 525                 530

GTA AAG AAG GGA AGC ATC TCA TTT GAG GAT CTG AAA GCT CAA AGT AAT     1747
Val Lys Lys Gly Ser Ile Ser Phe Glu Asp Leu Lys Ala Gln Ser Asn
    535                 540                 545

GAA GAG GTG GTT CAA CTT TCT CCA GAT GAG GAA ACT AAG GAC CTC ATT     1795
Glu Glu Val Val Gln Leu Ser Pro Asp Glu Glu Thr Lys Asp Leu Ile
550                 555                 560

CAT CGT CTC TTC CAT CCT GGG GAA CAT GTG AGG GAC TGT CTG AGT GAC     1843
His Arg Leu Phe His Pro Gly Glu His Val Arg Asp Cys Leu Ser Asp
565                 570                 575                 580

CTG CTG GGT CAT CCC TTC TTT TGG ACT TGG GAG AGC CGC TAT AGG ACG     1891
Leu Leu Gly His Pro Phe Phe Trp Thr Trp Glu Ser Arg Tyr Arg Thr
            585                 590                 595
```

```
CTT CGG AAT GTG GGA AAT GAA TCC GAC ATC AAA ACA CGA AAA TCT GAA     1939
Leu Arg Asn Val Gly Asn Glu Ser Asp Ile Lys Thr Arg Lys Ser Glu
            600                 605                 610

AGT GAG ATC CTC AGA CTA CTG CAA CCT GGG CCT TCT GAA CAT TCC AAA     1987
Ser Glu Ile Leu Arg Leu Leu Gln Pro Gly Pro Ser Glu His Ser Lys
        615                 620                 625

AGT TTT GAC AAG TGG ACG ACT AAG ATT AAT GAA TGT GTT ATG AAA AAA     2035
Ser Phe Asp Lys Trp Thr Thr Lys Ile Asn Glu Cys Val Met Lys Lys
    630                 635                 640

ATG AAT AAG TTT TAT GAA AAA AGA GGC AAT TTC TAC CAG AAC ACT GTG     2083
Met Asn Lys Phe Tyr Glu Lys Arg Gly Asn Phe Tyr Gln Asn Thr Val
645                 650                 655                 660

GGT GAT CTG CTA AAG TTC ATC CGG AAT TTG GGA GAA CAC ATT GAT GAA     2131
Gly Asp Leu Leu Lys Phe Ile Arg Asn Leu Gly Glu His Ile Asp Glu
                665                 670                 675

GAA AAG CAT AAA AAG ATG AAA TTA AAA ATT GGA GAC CCT TCC CTG TAT     2179
Glu Lys His Lys Lys Met Lys Leu Lys Ile Gly Asp Pro Ser Leu Tyr
            680                 685                 690

TTT CAG AAG ACA TTT CCA GAT CTG GTG ATC TAT GTC TAC ACA AAA CTA     2227
Phe Gln Lys Thr Phe Pro Asp Leu Val Ile Tyr Val Tyr Thr Lys Leu
        695                 700                 705

CAG AAC ACA GAA TAT AGA AAG CAT TTC CCC CAA ACC CAC AGT CCA AAC     2275
Gln Asn Thr Glu Tyr Arg Lys His Phe Pro Gln Thr His Ser Pro Asn
    710                 715                 720

AAA CCT CAG TGT GAT GGA GCT GGT GGG GCC AGT GGG TTG GCC AGC CCT     2323
Lys Pro Gln Cys Asp Gly Ala Gly Gly Ala Ser Gly Leu Ala Ser Pro
725                 730                 735                 740

GGG TGCTGATGGA CTGATTTGCT GGAGTTCAGG GAACTACTTA TTAGCTGTAG          2376
Gly

AGTCCTTGGC AAATCACAAC ATTCTGGGCC TTTTAACTCA CCAGGTTGCT TGTGAGGGAT   2436

GAGTTGCATA GCTGATATGT CAGTCCCTGG CATCGTGTAT TCCATATGTC TATAACAAAA   2496

GCAATATATA CCCAGACTAC ACTAGTCCAT AAGCTTTACC CACTAACTGG GAGGACATTC   2556

TGCTAAGATT CCTTTTGTCA ATTGCACCAA AGAATGAGT GCCTTGACCC CTAATGCTGC    2616

ATATGTTACA ATTCTCTCAC TTAATTTTCC CAATGATCTT GCAAAACAGG GATTATCATC   2676

CCCATTTAAG AACTGAGGAA CCTGAGACTC AGAGAGTGTG AGCTACTGGC CAAGATTAT    2736

TCAATTTATA CCTAGCACTT TATAAATTTA TGTGGTGTTA TTGGTACCTC TCATTTGGGC   2796

ACCTTAAAAC TTAACTATCT TCCAGGGCTC TTCCAGATGA GGCCCAAAAC ATATATAGGG   2856

GTTCCAGGAA TCTCATTCAT TCATTCAGTA TTTATTGAGC ATCTAGTATA AGTCTGGGCA   2916

CTGGATGCAT GAATT                                                   2931

(2) INFORMATION FOR SEQ ID NO:2:

(i) SEQUENCE CHARACTERISTICS:
        (A) LENGTH: 741 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Ser Arg Asp His Asn Asn Pro Gln Glu Gly Pro Thr Ser Ser
1               5                   10                  15

Ser Gly Arg Arg Ala Ala Val Glu Asp Asn His Leu Leu Ile Lys Ala
            20                  25                  30

Val Gln Asn Glu Asp Val Asp Leu Val Gln Gln Leu Leu Glu Gly Gly
        35                  40                  45
```

-continued

Ala Asn Val Asn Phe Gln Glu Glu Gly Gly Trp Thr Pro Leu His
 50                      55                   60

Asn Ala Ala Val Gln Met Ser Arg Glu Asp Ile Val Glu Leu Leu Leu
 65                  70                  75                   80

Arg His Gly Ala Asp Pro Val Leu Arg Lys Lys Asn Gly Ala Thr Leu
                 85                   90                  95

Phe Ile Leu Ala Ala Ile Ala Gly Ser Val Lys Leu Leu Lys Leu Phe
             100                 105                 110

Leu Ser Lys Gly Ala Asp Val Asn Glu Cys Asp Phe Tyr Gly Phe Thr
         115                 120                 125

Ala Phe Met Glu Ala Ala Val Tyr Gly Lys Val Lys Ala Leu Lys Phe
     130                 135                 140

Leu Tyr Lys Arg Gly Ala Asn Val Asn Leu Arg Arg Lys Thr Lys Glu
145                 150                 155                 160

Asp Gln Glu Arg Leu Arg Lys Gly Gly Ala Thr Ala Leu Met Asp Ala
                 165                 170                 175

Ala Glu Lys Gly His Val Glu Val Leu Lys Ile Leu Leu Asp Glu Met
             180                 185                 190

Gly Ala Asp Val Asn Ala Cys Asp Asn Met Gly Arg Asn Ala Leu Ile
         195                 200                 205

His Ala Leu Leu Ser Ser Asp Ser Asp Val Glu Ala Ile Thr His
     210                 215                 220

Leu Leu Leu Asp His Gly Ala Asp Val Asn Val Arg Gly Glu Arg Gly
225                 230                 235                 240

Lys Thr Pro Leu Ile Leu Ala Val Glu Lys Lys His Leu Gly Leu Val
                 245                 250                 255

Gln Arg Leu Leu Glu Gln Glu His Ile Glu Ile Asn Asp Thr Asp Ser
             260                 265                 270

Asp Gly Lys Thr Ala Leu Leu Leu Ala Val Glu Leu Lys Leu Lys Lys
         275                 280                 285

Ile Ala Glu Leu Leu Cys Lys Arg Gly Ala Ser Thr Asp Cys Gly Asp
     290                 295                 300

Leu Val Met Thr Ala Arg Arg Asn Tyr Asp His Ser Leu Val Lys Val
305                 310                 315                 320

Leu Leu Ser His Gly Ala Lys Glu Asp Phe His Pro Ala Glu Asp
                 325                 330                 335

Trp Lys Pro Gln Ser Ser His Trp Gly Ala Ala Leu Lys Asp Leu His
             340                 345                 350

Arg Ile Tyr Arg Pro Met Ile Gly Lys Leu Lys Phe Phe Ile Asp Glu
         355                 360                 365

Lys Tyr Lys Ile Ala Asp Thr Ser Glu Gly Gly Ile Tyr Leu Gly Phe
     370                 375                 380

Tyr Glu Lys Gln Glu Val Ala Val Lys Thr Phe Cys Glu Gly Ser Pro
385                 390                 395                 400

Arg Ala Gln Arg Glu Val Ser Cys Leu Gln Ser Ser Arg Glu Asn Ser
                 405                 410                 415

His Leu Val Thr Phe Tyr Gly Ser Glu Ser His Arg Gly His Leu Phe
             420                 425                 430

Val Cys Val Thr Leu Cys Glu Gln Thr Leu Glu Ala Cys Leu Asp Val
         435                 440                 445

His Arg Gly Glu Asp Val Glu Asn Glu Glu Asp Glu Phe Ser Arg Asn
     450                 455                 460

Val Leu Ser Ser Ile Phe Lys Ala Val Gln Glu Leu His Trp Ser Cys

-continued

```
465                  470                  475                  480
Gly Tyr Thr His Gln Asp Leu Gln Pro Gln Asn Ile Leu Ile Asp Ser
                485                  490                  495

Lys Lys Ala Ala His Leu Ala Asp Phe Asp Lys Ser Ile Lys Trp Ala
                500                  505                  510

Gly Asp Pro Gln Glu Val Lys Arg Asp Leu Glu Asp Leu Gly Arg Leu
                515                  520                  525

Val Leu Tyr Val Val Lys Lys Gly Ser Ile Ser Phe Glu Asp Leu Lys
                530                  535                  540

Ala Gln Ser Asn Glu Glu Val Val Gln Leu Ser Pro Asp Glu Glu Thr
545                  550                  555                  560

Lys Asp Leu Ile His Arg Leu Phe His Pro Gly Glu His Val Arg Asp
                565                  570                  575

Cys Leu Ser Asp Leu Leu Gly His Pro Phe Phe Trp Thr Trp Glu Ser
                580                  585                  590

Arg Tyr Arg Thr Leu Arg Asn Val Gly Asn Glu Ser Asp Ile Lys Thr
                595                  600                  605

Arg Lys Ser Glu Ser Glu Ile Leu Arg Leu Leu Gln Pro Gly Pro Ser
                610                  615                  620

Glu His Ser Lys Ser Phe Asp Lys Trp Thr Thr Lys Ile Asn Glu Cys
625                  630                  635                  640

Val Met Lys Lys Met Asn Lys Phe Tyr Glu Lys Arg Gly Asn Phe Tyr
                645                  650                  655

Gln Asn Thr Val Gly Asp Leu Leu Lys Phe Ile Arg Asn Leu Gly Glu
                660                  665                  670

His Ile Asp Glu Glu Lys His Lys Met Lys Leu Lys Ile Gly Asp
                675                  680                  685

Pro Ser Leu Tyr Phe Gln Lys Thr Phe Pro Asp Leu Val Ile Tyr Val
                690                  695                  700

Tyr Thr Lys Leu Gln Asn Thr Glu Tyr Arg Lys His Phe Pro Gln Thr
705                  710                  715                  720

His Ser Pro Asn Lys Pro Gln Cys Asp Gly Ala Gly Gly Ala Ser Gly
                725                  730                  735

Leu Ala Ser Pro Gly
                740
```

(2) INFORMATION FOR SEQ ID NO:3:

(i) SEQUENCE CHARACTERISTICS:
        (A) LENGTH: 2200 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 164..2200

(xi) SEQUENCE DESCRIPTION: SEQ ID NO:3:

```
ATTCGGCACG AGGAAGGTGC CAATTACTAG CTCCCTTCTT TATTCGTGTA CTGATGAGAT      60

GTCAGAAGAC AGAACATAAT CAGCCCAATC CCTACTCCAA GACTCTCATT GTGTCCCAAA    120

GAAACACACG TGTGCATTTC CCAAGGAAAA GGCATTGAGG ACC ATG GAG ACC CCG      175
                                              Met Glu Thr Pro
```

-continued

1

| | | |
|---|---|---|
| GAT TAT AAC ACA CCT CAG GGT GGA ACC CCA TCA GCG GGA AGT CAG AGG<br>Asp Tyr Asn Thr Pro Gln Gly Gly Thr Pro Ser Ala Gly Ser Gln Arg<br>5                      10                      15               20 | | 223 |
| ACC GTT GTC GAA GAT GAT TCT TCG TTG ATC AAA GCT GTT CAG AAG GGA<br>Thr Val Val Glu Asp Asp Ser Ser Leu Ile Lys Ala Val Gln Lys Gly<br>                      25                      30                      35 | | 271 |
| GAT GTT GTC AGG GTC CAG CAA TTG TTA GAA AAA GGG GCT GAT GCC AAT<br>Asp Val Val Arg Val Gln Gln Leu Leu Glu Lys Gly Ala Asp Ala Asn<br>                 40                      45                      50 | | 319 |
| GCC TGT GAA GAC ACC TGG GGC TGG ACA CCT TTG CAC AAC GCA GTG CAA<br>Ala Cys Glu Asp Thr Trp Gly Trp Thr Pro Leu His Asn Ala Val Gln<br>        55                      60                      65 | | 367 |
| GCT GGC AGG GTA GAC ATT GTG AAC CTC CTG CTT AGT CAT GGT GCT GAC<br>Ala Gly Arg Val Asp Ile Val Asn Leu Leu Leu Ser His Gly Ala Asp<br>    70                      75                      80 | | 415 |
| CCT CAT CGG AGG AAG AAG AAT GGG GCC ACC CCC TTC ATC ATT GCT GGG<br>Pro His Arg Arg Lys Lys Asn Gly Ala Thr Pro Phe Ile Ile Ala Gly<br>85                      90                      95               100 | | 463 |
| ATC CAG GGA GAT GTG AAA CTG CTC GAG ATT CTC CTC TCT TGT GGT GCA<br>Ile Gln Gly Asp Val Lys Leu Leu Glu Ile Leu Leu Ser Cys Gly Ala<br>                 105                     110                  115 | | 511 |
| GAC GTC AAT GAG TGT GAC GAG AAC GGA TTC ACG GCT TTC ATG GAA GCT<br>Asp Val Asn Glu Cys Asp Glu Asn Gly Phe Thr Ala Phe Met Glu Ala<br>           120                     125                  130 | | 559 |
| GCT GAG CGT GGT AAC GCT GAA GCC TTA AGA TTC CTT TTT GCT AAG GGA<br>Ala Glu Arg Gly Asn Ala Glu Ala Leu Arg Phe Leu Phe Ala Lys Gly<br>       135                     140                   145 | | 607 |
| GCC AAT GTG AAT TTG CGA CGA CAG ACA ACG AAG GAC AAA AGG CGA TTG<br>Ala Asn Val Asn Leu Arg Arg Gln Thr Thr Lys Asp Lys Arg Arg Leu<br>   150                      155                     160 | | 655 |
| AAG CAA GGA GGC GCC ACA GCT CTC ATG AGC GCT GCT GAG AAG GGC CAC<br>Lys Gln Gly Gly Ala Thr Ala Leu Met Ser Ala Ala Glu Lys Gly His<br>165                     170                     175                  180 | | 703 |
| CTG GAA GTC CTG AGA ATT CTC CTC AAT GAC ATG AAG GCA GAA GTC GAT<br>Leu Glu Val Leu Arg Ile Leu Leu Asn Asp Met Lys Ala Glu Val Asp<br>                 185                     190                  195 | | 751 |
| GCT CGG GAC AAC ATG GGC AGA AAT GCC CTG ATC CGT ACT CTG CTG AAC<br>Ala Arg Asp Asn Met Gly Arg Asn Ala Leu Ile Arg Thr Leu Leu Asn<br>           200                     205                  210 | | 799 |
| TGG GAT TGT GAA AAT GTG GAG GAG ATT ACT TCA ATC CTG ATT CAG CAC<br>Trp Asp Cys Glu Asn Val Glu Glu Ile Thr Ser Ile Leu Ile Gln His<br>       215                     220                   225 | | 847 |
| GGG GCT GAT GTT AAC TGT AGA GGA GAA AGA GGG AAA ACA CCC CTC ATC<br>Gly Ala Asp Val Asn Cys Arg Gly Glu Arg Gly Lys Thr Pro Leu Ile<br>   230                      235                     240 | | 895 |
| GCA GCA GTG GAG AGG AAG CAC ACA GGC TTG GTG CAG ATG CTC CTG AGT<br>Ala Ala Val Glu Arg Lys His Thr Gly Leu Val Gln Met Leu Leu Ser<br>245                     250                     255                  260 | | 943 |
| CGG GAA GGC ATA AAC ATA GAT GCC AGG GAT AAC GAG GGC AAG ACA GCT<br>Arg Glu Gly Ile Asn Ile Asp Ala Arg Asp Asn Glu Gly Lys Thr Ala<br>                 265                     270                  275 | | 991 |
| CTG CTA ATT GCT GTT GAT AAA CAA CTG AAG GAA ATT GTC CAG TTG CTT<br>Leu Leu Ile Ala Val Asp Lys Gln Leu Lys Glu Ile Val Gln Leu Leu<br>           280                     285                  290 | | 1039 |
| CTT GAA AAG GGA GCT GAT AAG TGT GAC GAT CTT GTT TGG ATA GCC AGG<br>Leu Glu Lys Gly Ala Asp Lys Cys Asp Asp Leu Val Trp Ile Ala Arg<br>       295                     300                   305 | | 1087 |
| AGG AAT CAT GAC TAT CAC CTT GTA AAG CTT CTC CTC CCT TAT GTA GCT<br>Arg Asn His Asp Tyr His Leu Val Lys Leu Leu Leu Pro Tyr Val Ala | | 1135 |

-continued

|  |  | 310 |  |  | 315 |  |  | 320 |  |  |  |  |  |  |  |
|---|---|---|---|---|---|---|---|---|---|---|---|---|---|---|---|
| AAT | CCT | GAC | ACC | GAC | CCT | CCT | GCT | GGA | GAC | TGG | TCG | CCT | CAC | AGT | TCA | 1183 |
| Asn | Pro | Asp | Thr | Asp | Pro | Pro | Ala | Gly | Asp | Trp | Ser | Pro | His | Ser | Ser |  |
| 325 |  |  |  | 330 |  |  |  |  | 335 |  |  |  |  | 340 |  |  |

| CGT | TGG | GGG | ACA | GCC | TTG | AAA | AGC | CTC | CAC | AGT | ATG | ACT | CGA | CCC | ATG | 1231 |
| Arg | Trp | Gly | Thr | Ala | Leu | Lys | Ser | Leu | His | Ser | Met | Thr | Arg | Pro | Met |  |
|  |  |  |  |  | 345 |  |  |  |  | 350 |  |  |  |  | 355 |  |

| ATT | GGC | AAA | CTC | AAG | ATC | TTC | ATT | CAT | GAT | GAC | TAT | AAA | ATT | GCT | GGC | 1279 |
| Ile | Gly | Lys | Leu | Lys | Ile | Phe | Ile | His | Asp | Asp | Tyr | Lys | Ile | Ala | Gly |  |
|  |  |  |  | 360 |  |  |  |  | 365 |  |  |  |  | 370 |  |  |

| ACT | TCC | GAA | GGG | GCT | GTC | TAC | CTA | GGG | ATC | TAT | GAC | AAT | CGA | GAA | GTG | 1327 |
| Thr | Ser | Glu | Gly | Ala | Val | Tyr | Leu | Gly | Ile | Tyr | Asp | Asn | Arg | Glu | Val |  |
|  |  | 375 |  |  |  |  | 380 |  |  |  |  | 385 |  |  |  |  |

| GCT | GTG | AAG | GTC | TTC | CGT | GAG | AAT | AGC | CCA | CGT | GGA | TGT | AAG | GAA | GTC | 1375 |
| Ala | Val | Lys | Val | Phe | Arg | Glu | Asn | Ser | Pro | Arg | Gly | Cys | Lys | Glu | Val |  |
|  | 390 |  |  |  |  | 395 |  |  |  |  | 400 |  |  |  |  |  |

| TCT | TGT | CTG | CGG | GAC | TGC | GGT | GAC | CAC | AGT | AAC | TTA | GTG | GCT | TTC | TAT | 1423 |
| Ser | Cys | Leu | Arg | Asp | Cys | Gly | Asp | His | Ser | Asn | Leu | Val | Ala | Phe | Tyr |  |
| 405 |  |  |  |  | 410 |  |  |  |  | 415 |  |  |  |  | 420 |  |

| GGA | AGA | GAG | GAC | GAT | AAG | GGC | TGT | TTA | TAT | GTG | TGT | GTG | TCC | CTG | TGT | 1471 |
| Gly | Arg | Glu | Asp | Asp | Lys | Gly | Cys | Leu | Tyr | Val | Cys | Val | Ser | Leu | Cys |  |
|  |  |  |  | 425 |  |  |  |  | 430 |  |  |  |  | 435 |  |  |

| GAG | TGG | ACA | CTG | GAA | GAG | TTC | CTG | AGG | TTG | CCC | AGA | GAG | GAA | CCT | GTG | 1519 |
| Glu | Trp | Thr | Leu | Glu | Glu | Phe | Leu | Arg | Leu | Pro | Arg | Glu | Glu | Pro | Val |  |
|  |  |  | 440 |  |  |  |  | 445 |  |  |  |  | 450 |  |  |  |

| GAG | AAC | GGG | GAA | GAT | AAG | TTT | GCC | CAC | AGC | ATC | CTA | TTA | TCT | ATA | TTT | 1567 |
| Glu | Asn | Gly | Glu | Asp | Lys | Phe | Ala | His | Ser | Ile | Leu | Leu | Ser | Ile | Phe |  |
|  |  |  | 455 |  |  |  |  | 460 |  |  |  |  | 465 |  |  |  |

| GAG | GGT | GTT | CAA | AAA | CTA | CAC | TTG | CAT | GGA | TAT | TCC | CAT | CAG | GAC | CTG | 1615 |
| Glu | Gly | Val | Gln | Lys | Leu | His | Leu | His | Gly | Tyr | Ser | His | Gln | Asp | Leu |  |
|  | 470 |  |  |  |  | 475 |  |  |  |  | 480 |  |  |  |  |  |

| CAA | CCA | CAA | AAC | ATC | TTA | ATA | GAT | TCC | AAG | AAA | GCT | GTC | CGG | CTG | GCA | 1663 |
| Gln | Pro | Gln | Asn | Ile | Leu | Ile | Asp | Ser | Lys | Lys | Ala | Val | Arg | Leu | Ala |  |
| 485 |  |  |  | 490 |  |  |  |  | 495 |  |  |  |  | 500 |  |  |

| GAT | TTT | GAT | CAG | AGC | ATC | CGA | TGG | ATG | GGA | GAG | TCA | CAG | ATG | GTC | AGG | 1711 |
| Asp | Phe | Asp | Gln | Ser | Ile | Arg | Trp | Met | Gly | Glu | Ser | Gln | Met | Val | Arg |  |
|  |  |  |  | 505 |  |  |  |  | 510 |  |  |  |  | 515 |  |  |

| AGA | GAC | TTG | GAG | GAT | CTT | GGA | CGG | CTG | GTT | CTC | TAC | GTG | GTA | ATG | AAA | 1759 |
| Arg | Asp | Leu | Glu | Asp | Leu | Gly | Arg | Leu | Val | Leu | Tyr | Val | Val | Met | Lys |  |
|  |  | 520 |  |  |  |  | 525 |  |  |  |  | 530 |  |  |  |  |

| GGT | GAG | ATC | CCC | TTT | GAG | ACA | CTA | AAG | ACT | CAG | AAT | GAT | GAA | GTG | CTG | 1807 |
| Gly | Glu | Ile | Pro | Phe | Glu | Thr | Leu | Lys | Thr | Gln | Asn | Asp | Glu | Val | Leu |  |
|  |  | 535 |  |  |  |  | 540 |  |  |  |  | 545 |  |  |  |  |

| CTT | ACA | ATG | TCT | CCA | GAT | GAG | GAG | ACT | AAG | GAC | CTC | ATT | CAT | TGC | CTG | 1855 |
| Leu | Thr | Met | Ser | Pro | Asp | Glu | Glu | Thr | Lys | Asp | Leu | Ile | His | Cys | Leu |  |
| 550 |  |  |  |  | 555 |  |  |  |  | 560 |  |  |  |  |  |  |

| TTT | TCT | CCT | GGA | GAA | AAT | GTC | AAG | AAC | TGC | CTG | GTA | GAC | CTG | CTT | GGC | 1903 |
| Phe | Ser | Pro | Gly | Glu | Asn | Val | Lys | Asn | Cys | Leu | Val | Asp | Leu | Leu | Gly |  |
| 565 |  |  |  | 570 |  |  |  |  | 575 |  |  |  |  | 580 |  |  |

| CAT | CCT | TTC | TTT | TGG | ACT | TGG | GAG | AAC | CGC | TAT | AGA | ACA | CTC | CGG | AAT | 1951 |
| His | Pro | Phe | Phe | Trp | Thr | Trp | Glu | Asn | Arg | Tyr | Arg | Thr | Leu | Arg | Asn |  |
|  |  |  |  | 585 |  |  |  |  | 590 |  |  |  |  | 595 |  |  |

| GTG | GGA | AAT | GAA | TCT | GAC | ATC | AAA | GTA | CGG | AAA | TGT | AAA | AGT | GAT | CTT | 1999 |
| Val | Gly | Asn | Glu | Ser | Asp | Ile | Lys | Val | Arg | Lys | Cys | Lys | Ser | Asp | Leu |  |
|  |  |  | 600 |  |  |  |  | 605 |  |  |  |  | 610 |  |  |  |

| CTC | AGA | CTA | CTG | CAG | CAT | CAG | ACA | CTT | GAG | CCT | CCC | AGA | AGC | TTT | GAC | 2047 |
| Leu | Arg | Leu | Leu | Gln | His | Gln | Thr | Leu | Glu | Pro | Pro | Arg | Ser | Phe | Asp |  |
|  |  | 615 |  |  |  |  | 620 |  |  |  |  | 625 |  |  |  |  |

| CAG | TGG | ACA | TCT | AAG | ATC | GAC | AAA | AAT | GTT | ATG | GAT | GAA | ATG | AAT | CAT | 2095 |
| Gln | Trp | Thr | Ser | Lys | Ile | Asp | Lys | Asn | Val | Met | Asp | Glu | Met | Asn | His |  |

```
                      630                635                640
TTC TAC GAA AAG AGA AAA AAA AAC CCT TAT CAG GAT ACT GTA GGT GAT    2143
Phe Tyr Glu Lys Arg Lys Lys Asn Pro Tyr Gln Asp Thr Val Gly Asp
645                 650                 655                 660

CTG CTG AAG TTT ATT CGG AAT ATA GGC GAA CAC ATC AAT GAG GAA AAA    2191
Leu Leu Lys Phe Ile Arg Asn Ile Gly Glu His Ile Asn Glu Glu Lys
                665                 670                 675

AAG CGG GGG                                                        2200
Lys Arg Gly
```

(2) INFORMATION FOR SEQ ID NO:4:

(i) SEQUENCE CHARACTERISTICS:
        (A) LENGTH: 679 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Thr Pro Asp Tyr Asn Thr Pro Gln Gly Gly Thr Pro Ser Ala
 1               5                  10                  15

Gly Ser Gln Arg Thr Val Val Glu Asp Asp Ser Ser Leu Ile Lys Ala
                20                  25                  30

Val Gln Lys Gly Asp Val Val Arg Val Gln Gln Leu Leu Glu Lys Gly
            35                  40                  45

Ala Asp Ala Asn Ala Cys Glu Asp Thr Trp Gly Trp Thr Pro Leu His
        50                  55                  60

Asn Ala Val Gln Ala Gly Arg Val Asp Ile Val Asn Leu Leu Leu Ser
65                  70                  75                  80

His Gly Ala Asp Pro His Arg Arg Lys Lys Asn Gly Ala Thr Pro Phe
                85                  90                  95

Ile Ile Ala Gly Ile Gln Gly Asp Val Lys Leu Leu Glu Ile Leu Leu
            100                 105                 110

Ser Cys Gly Ala Asp Val Asn Glu Cys Asp Glu Asn Gly Phe Thr Ala
        115                 120                 125

Phe Met Glu Ala Ala Glu Arg Gly Asn Ala Glu Ala Leu Arg Phe Leu
    130                 135                 140

Phe Ala Lys Gly Ala Asn Val Asn Leu Arg Arg Gln Thr Thr Lys Asp
145                 150                 155                 160

Lys Arg Arg Leu Lys Gln Gly Gly Ala Thr Ala Leu Met Ser Ala Ala
                165                 170                 175

Glu Lys Gly His Leu Glu Val Leu Arg Ile Leu Leu Asn Asp Met Lys
            180                 185                 190

Ala Glu Val Asp Ala Arg Asp Asn Met Gly Arg Asn Ala Leu Ile Arg
        195                 200                 205

Thr Leu Leu Asn Trp Asp Cys Glu Asn Val Glu Glu Ile Thr Ser Ile
    210                 215                 220

Leu Ile Gln His Gly Ala Asp Val Asn Cys Arg Gly Glu Arg Gly Lys
225                 230                 235                 240

Thr Pro Leu Ile Ala Ala Val Glu Arg Lys His Thr Gly Leu Val Gln
                245                 250                 255

Met Leu Leu Ser Arg Glu Gly Ile Asn Ile Asp Ala Arg Asp Asn Glu
            260                 265                 270

Gly Lys Thr Ala Leu Leu Ile Ala Val Asp Lys Gln Leu Lys Glu Ile
        275                 280                 285

Val Gln Leu Leu Leu Glu Lys Gly Ala Asp Lys Cys Asp Asp Leu Val
```

-continued

```
            290                 295                 300
Trp Ile Ala Arg Arg Asn His Asp Tyr His Leu Val Lys Leu Leu Leu
305                 310                 315                 320

Pro Tyr Val Ala Asn Pro Asp Thr Asp Pro Pro Ala Gly Asp Trp Ser
                    325                 330                 335

Pro His Ser Ser Arg Trp Gly Thr Ala Leu Lys Ser Leu His Ser Met
                    340                 345                 350

Thr Arg Pro Met Ile Gly Lys Leu Lys Ile Phe Ile His Asp Asp Tyr
                355                 360                 365

Lys Ile Ala Gly Thr Ser Glu Gly Ala Val Tyr Leu Gly Ile Tyr Asp
            370                 375                 380

Asn Arg Glu Val Ala Val Lys Val Phe Arg Glu Asn Ser Pro Arg Gly
385                 390                 395                 400

Cys Lys Glu Val Ser Cys Leu Arg Asp Cys Gly Asp His Ser Asn Leu
                    405                 410                 415

Val Ala Phe Tyr Gly Arg Glu Asp Asp Lys Gly Cys Leu Tyr Val Cys
                420                 425                 430

Val Ser Leu Cys Glu Trp Thr Leu Glu Glu Phe Leu Arg Leu Pro Arg
            435                 440                 445

Glu Glu Pro Val Glu Asn Gly Glu Asp Lys Phe Ala His Ser Ile Leu
450                 455                 460

Leu Ser Ile Phe Glu Gly Val Gln Lys Leu His Leu His Gly Tyr Ser
465                 470                 475                 480

His Gln Asp Leu Gln Pro Gln Asn Ile Leu Ile Asp Ser Lys Lys Ala
                485                 490                 495

Val Arg Leu Ala Asp Phe Asp Gln Ser Ile Arg Trp Met Gly Glu Ser
                500                 505                 510

Gln Met Val Arg Arg Asp Leu Glu Asp Leu Gly Arg Leu Val Leu Tyr
            515                 520                 525

Val Val Met Lys Gly Glu Ile Pro Phe Glu Thr Leu Lys Thr Gln Asn
530                 535                 540

Asp Glu Val Leu Leu Thr Met Ser Pro Asp Glu Glu Thr Lys Asp Leu
545                 550                 555                 560

Ile His Cys Leu Phe Ser Pro Gly Glu Asn Val Lys Asn Cys Leu Val
                565                 570                 575

Asp Leu Leu Gly His Pro Phe Phe Trp Thr Trp Glu Asn Arg Tyr Arg
                580                 585                 590

Thr Leu Arg Asn Val Gly Asn Glu Ser Asp Ile Lys Val Arg Lys Cys
            595                 600                 605

Lys Ser Asp Leu Leu Arg Leu Leu Gln His Gln Thr Leu Glu Pro Pro
610                 615                 620

Arg Ser Phe Asp Gln Trp Thr Ser Lys Ile Asp Lys Asn Val Met Asp
625                 630                 635                 640

Glu Met Asn His Phe Tyr Glu Lys Arg Lys Asn Pro Tyr Gln Asp
                645                 650                 655

Thr Val Gly Asp Leu Leu Lys Phe Ile Arg Asn Ile Gly Glu His Ile
                660                 665                 670

Asn Glu Glu Lys Lys Arg Gly
            675
```